US007456011B2

(12) United States Patent
Liu et al.

(10) Patent No.: US 7,456,011 B2
(45) Date of Patent: Nov. 25, 2008

(54) MODIFIED CYANOVIRIN-N POLYPEPTIDE

(75) Inventors: Xiaowen Liu, Cupertino, CA (US);
Kirsten Essenmacher, Palo Alto, CA (US); David A. Simpson, Redwood City, CA (US); Qiang Xu, Cupertino, CA (US)

(73) Assignee: Osel, Inc., Santa Clara, CA (US)

( * ) Notice: Subject to any disclaimer, the term of this patent is extended or adjusted under 35 U.S.C. 154(b) by 0 days.

(21) Appl. No.: 11/331,965

(22) Filed: Jan. 12, 2006

(65) Prior Publication Data

US 2006/0194226 A1    Aug. 31, 2006

Related U.S. Application Data

(60) Provisional application No. 60/643,613, filed on Jan. 12, 2005.

(51) Int. Cl.
*A01N 63/00* (2006.01)
*A61K 39/02* (2006.01)
*C12N 1/22* (2006.01)
*C07K 1/00* (2006.01)

(52) U.S. Cl. .............. 435/252.3; 424/93.45; 424/200.1; 530/402

(58) Field of Classification Search ........................ None
See application file for complete search history.

(56) References Cited

U.S. PATENT DOCUMENTS

| | | | |
|---|---|---|---|
| 5,705,160 | A | 1/1998 | Bruce et al. |
| 5,733,540 | A | 3/1998 | Lee |
| 5,804,179 | A | 9/1998 | Bruce et al. |
| 5,821,081 | A | 10/1998 | Boyd et al. |
| 5,821,088 | A | 10/1998 | Darzins et al. |
| 6,180,100 | B1 | 1/2001 | Bruce et al. |
| 6,193,982 | B1 | 2/2001 | Boyd |
| 6,277,370 | B1 | 8/2001 | Cavaliere Ved. Vesely et al. |
| 7,179,458 | B2 * | 2/2007 | Chang et al. ............... 424/93.2 |
| 2004/0038340 | A1 * | 2/2004 | Deutscher et al. .......... 435/69.1 |

FOREIGN PATENT DOCUMENTS

| WO | WO 96/11277 A1 | 4/1996 |
|---|---|---|
| WO | WO 2004/007695 A2 | 1/2004 |

OTHER PUBLICATIONS

Avall-Jaaskelainen, Silja et al.; "Surface Display of the Receptor-Binding Region of the *Lactobacillus brevis* S-Layer Protein in *Lactococcus lactis* Provides Nonadhesive *Lactococci* with the Ability to Adhere to Intestinal Epithelial Cells"; 2003, *Applied and Environmental Microbiology*, vol. 69, No. 4, pp. 2230-2236.
Barrientos, Laura G., et al., "Solution Structure of a Circular-Permuted Variant of the Potent HIV-Inactivating Protein Cyanovirin-N: Structural Basis for Protein Stability and Oligosaccharide Interaction;" *Journal of Molecular Biology*; 2003; vol. 325; pp. 211-223.

Beninati, Concetta, et al., "Therapy of Mucosal Candidiasis by Expression of an Anti-Idiotype in Human Commensal Bacteria;" Oct. 2000; *Nature Biotechnology*; vol. 18; pp. 1060-1064.
Boyd, Michael R., et al., "Discovery of Cyanovirin-N, a Novel Human Immunodeficiency Virus-Inactivating Protein that Binds Viral Surfce Envelope Glycoprotein gp120: Potential Applications to Microbicide Development;" Jul. 1997; *Antimicrobial Agents and Chemotherapy*; vol. 41; pp. 1521-1530.
Bringel, Francoise, et al.; "Characterization, Cloning, Curing, and Distribution in Lactic Acid Bacteria of pLP1, a Plasmid from *Lactobacillus* Plantarum CCM 1904 and its Use in Shuttle Vector Construction;" 1989; *Plasmid*; vol. 22; 193-202.
Buckley, Nicole D., et al.; "An Effective Strategy, Applicable to Streptococcus Salivarious and Related Bacteria, to Enhance or Confer Electroporation Competence;" Sep. 1999; *Applied and Environmental Microbiology*; vol. 66; No. 9; pp. 3800-3804.
Giomarelli, Barbara et al.; "The microbicide cyanovirin-N expressed on the surface of commensal bacterium *Streptococcus gordonii* captures HIV-1"; 2002, *AIDS Concise Communication*, vol. 16, No. 10, pp. 1351-1356.
Kim, Y.H., et al.; "Optimization of Technical Conditions for the Transformation of *Lactobacillus acidophilus* Strains by Elecroporation;" 2005; *Journal of Applied Microbiology*; vol. 99; pp. 167-174.
Kruger, Carina, et al.; "In Situ Delivery of Passive Immunity by *Lactobacilli* Producing Single-Chain Antibodies;" Jul. 2002; *Nature Biotechnology*; vol. 20; pp. 702-706.
Liu, Janice J. et al.; "Activity of HIV entry and fusion inhibitors expressed by the human vaginal colonizing probiotic *Lactobacillus reuteri* RC-14"; 2006, *Cellular Microbiology* , pp. 1-11.
Luchansky, John, B., et al.; "Molecular Cloning and Deoxyribonucleic Acid Polymorphisms in *Lactobacillus acidophilus* Gasseri;" 1991; *Journal of Dairy Science*; vol. 74; pp. 3293-3302.
Maggi, Tiziana et al.; "Genetic engineering of *Streptococcus gordonii* for the simultaneous display of two heterologous proteins at the bacterial surface"; 2002, *FEMS Microbiology Letters*, vol. 210, pp. 135-141.
Mori, Toshiyuki, et al., "Functional Homologs of Cyanovirin-N Amenable to Mass Production in Prokaryotic and Eukaryotic Hosts;" *Protein Expression and Purification*; 2002; vol. 26, pp. 42-49.

(Continued)

*Primary Examiner*—Bruce Campell
*Assistant Examiner*—Benjamin P Blumel

(74) *Attorney, Agent, or Firm*—Townsend and Townsend and Crew LLP

(57) ABSTRACT

This disclosure relates to a modified version of cyanovirin-N protein and a transformed *Lactobacillus* bacterium that is capable of recombinantly expressing this modified protein. Further disclosed are polynucleotide sequence encoding the modified cyanovirin-N protein, expression cassette that allows the expression of the modified protein, and method of make and use of the modified protein as well as the transformed *Lactobacillus* bacterium. In addition, this disclosure describes two novel promoters originated from *L. jensenii*, which are capable of directing a high level of gene expression in *Lactobacillus* bacteria. Also described are an expression cassette comprising one of the novel promoters, a genetically modified *Lactobacillus* bacterium containing the expression cassette, a method for recombinant gene expression in *Lactobacillus* bacteria using the novel promoters, and a method for delivery of proteins with desired biological activity to a mucosal surface in a human.

17 Claims, 7 Drawing Sheets

OTHER PUBLICATIONS

Mason, Charlene K., "Modified Electroporation Protocol for *Lactobacilli* Isolated from the Chicken Coop Facilities Transformation and the Use of Genetic Tool;" 2005; *Journal of Microbiological Methods*; vol. 60; pp. 353-363.

Navarre, William Wley et al.; "Surface Proteins of Gram-Positive Bacteria and Mechanisms of Their Targeting to the Cell Wall Envelope"; 1999, *Microbiology and Molecular Biology Reviews*, vol. 63, No. 1, pp. 174-229.

O'Keefe, Barry R., et al., "Analysis of the Interaction Between the HIV-Inactivating Protein Cyanovirin-N and Soluable Forms of the Envelope Glycoproteins gp 120 and gp41;" 2000; *Mol. Pharmacol*.; vol. 58; pp. 982-992.

Pallen, Mark J. et al.; "An embarrassment of sortases—a richness of substrates?"; 2001, *Trends in Microbiology*, vol. 9, No. 3, pp. 97-100.

Samuelson, Patrik et al.; "Display of proteins on bacteria"; 2002, *Journal of Biotechnology*, vol. 96, pp. 129-154.

Shenoy, Shilpa, R., et al., "Selective Interactions of the Human Immunodeficiency Virus-Inactivating Protein Cyanovirin-N with High -Mannose Oligosaccharides on gp 120 and other Glyciproteins;" 2001; *J. Pharmacol. Exp. Ther*.; vol. 297; pp. 704-710.

Steidler, Lothar, et al.; "Treatment of Murine Colitis by *Lactococcus lactis* Secreting Interleukin-10;" Aug. 25, 2002; *Science*; vol. 289; pp. 1352-1355.

Strauss, Andreas et al.; "In vivo immobilization of enzymatically active polypeptides on the cell surface of *Staphylococcus camosus*"; 1996, *Molecular Microbiology*, vol. 21, No. 3, pp. 491-5000.

Schneewind, Olaf et al.; "Sorting of Protein A to the Staphlococcal Cell Wall"; 1992, *Cell*, vol. 70, pp. 267-281.

That, Hung Ton et al.; "An embarrassment of sortases—a richness of substrates?"; 2001, *Trends in Microbiology*, vol. 9, No. 3, pp. 101.

Turner, Mark S. et al.; "Peptide Surface Display and Secretion Using Two LPXTG-Containing Surface Proteins from *Lactobacillus fermentum* BR11"; 2003, *Applied and Environmental Microbiology*, vol. 69, No. 10, pp. 5855-5863.

Wei, Ming-Qian, et al.; "An Improved Method for the Transformation of *Lactobacillus* Strains Using Electroporation;" 1995; *Journal of Microbiology Methods*; vol. 21; pp. 97-109.

Vallor, Ana C., et al., "Factors Associated with Acquistion of, or Persistent Colonization by, Vaginal *Lactobacilli*: Role of Hydrogen Peroxide Production;" 2001, *The Journal of Infection Diseases*; vol. 184; pp. 1431-1436.

Van Der Vossen, Jos M.B.M., et al., "Isolation and Characterization of *Streptococcus cremoris* Wg2-Specific Promoters;" Oct. 1997; *Applied and Environmental Microbiology*; vol. 53; No. 10; pp. 2452-2457.

Medaglina, Donata, et al., "Vaginal Immunization with Recombinant Gram-Positive Bacteria;" 1998; *American Journal of Reproductive Immunology*; vol. 39; pp. 199-208.

Tsai, Che-Chung, et al., "Cyanovirin-N Inhibits AIDS Virus Infections in Vaginal Transmission Models," 2004; *AIDS Research and Human Retroviruses*; vol. 20; No. 1; pp. 11-18.

\* cited by examiner

*MKKNLRIVSAAAAALLAVAPVAASAVSTVSA*l¹gkfsqtcynsaiqgsvltstcertnggy ntssidlnsvienvdgslkwqg⁵¹snfietcrntqlagsselaaecktraqqfvstkinlddhianidgtlkye¹⁰¹

B

Predicted       Observed
                                          ↓             ↓

*MKKNLRIVSAAAAALLAVAPVAASAVSTVSA*l¹gkfsqtcynsaiqgs¹⁶vltstcertnggy
Removal of *cbsAss* ntssidlnsvienvdgslkwqg⁵¹snfietcrntqlagsselaaecktraqqfvstkinlddhianidgtlkye¹⁰¹

Figure 3 kDa

| | CV-N (PG) | Variants |
| --- | --- | --- |
| | | V17A  V17L  V17S |

62 —
49 —
38 —
28 —
17 —
14 —
 6 —
 3 —

Anti-CV-N

Figure 4

A. Purification of CV-N (FL)

| Sample | Ref Std | CV-N (FL) | | |
|---|---|---|---|---|
| Lane | 1 | 2 | 3 | 4 |
| kDa | | | | |
| 28 | — | | | |
| 17 | — | | | |
| 14 | — | | | |
| 6 | — | | | |

Coomassie blue staining

B. Anti-HIV assay

*Lactobacillus*-derived CV-N (μg/ml)

Figure 5

Coomassie blue staining

MODIFIED CYANOVIRIN-N POLYPEPTIDE

RELATED APPLICATIONS

This application claims priority to provisional U.S. patent application No. 60/643,613, filed on Jan. 12, 2005, the contents of which are incorporated herein by reference in the entirety.

STATEMENT AS TO RIGHTS TO INVENTIONS MADE UNDER FEDERALLY SPONSORED RESEARCH AND DEVELOPMENT

This invention was made with the U.S. government support under Grant Nos. 2 R44 AI46203-02 and U19 AI60615, awarded by the National Institutes of Health. The government has certain rights in this invention.

BACKGROUND OF THE INVENTION

Acquired Immune Deficiency Syndrome ("AIDS") is one of the most deadly diseases to affect human. This disease cripples a person's immune system, leaving the person susceptible to opportunistic infections, malignancies, or other pathological conditions against which a normal immune system would have protected the person. After one develops symptoms of AIDS, death generally occurs within 2-3 years of diagnosis. The etiology of AIDS and related disorders has been identified as being associated with infection by a class of lymphotrophic retrovirus termed human immunodeficiency virus (HIV), which is spread when body fluids, such as semen, vaginal fluids, or blood, from an infected individual are passed to another individual. Believed to have originated in Africa, HIV infection or AIDS is now a global epidemic. In the U.S. alone, there are an estimated over one million people who have been infected with HIV.

Because of the devastating effect of AIDS and the increasing spread of HIV infection around the world, much effort has been devoted to elucidate the mechanism of how HIV attacks the human immune system and identify new approaches for preventing HIV infection. It is now understood that two glycosylated HIV envelope proteins, gp120 and gp41, mediate the attachment of virions to cell surface receptor molecules (such as CD4), initiating the process of internalization of HIV into the cells. Because the binding of gp120 and CD4 is one crucial step in HIV infection of $CD4^+$ cells, many studies have focused on various strategies that block the gp120-CD4 binding.

On the other hand, it has been recognized that the predominant routine of HIV transmission is via sexual contact. Thus, there exists a need for new prophylactic methods that can effectively prevent HIV infection upon initial contact. This invention addresses this and other related needs.

BRIEF SUMMARY OF THE INVENTION

In a first aspect, the present invention relates to a *Lactobacillus* bacterium expressing a modified cyanovirin-N (CV-N) polypeptide. This modified CV-N polypeptide comprises a core amino acid sequence that is at least 90% identical to SEQ ID NO:1 and an additional amino acid sequence immediately to the N-terminus of the core amino acid sequence. The additional amino acid sequence consists of two to twenty, preferably up to fifteen, more preferably up to ten or six, amino acids, among which at least one of the first two amino acids is identical to the corresponding amino acid in the first two amino acids of a mature *Lactobacillus* protein following the cleavage of a signal sequence that is present in the precursor of the protein. In other words, the first or second amino acid in this additional amino acid sequence should be identical to the first or second amino acid in a mature *Lactobacillus* protein, respectively. The modified CV-N polypeptide is derived from a precursor polypeptide following the cleavage of the signal sequence. Furthermore, the modified CV-N polypeptide specifically binds to gp120 of human immunodeficiency virus (HIV) and inhibits the infectivity of HIV.

In some embodiments, the *Lactobacillus* protein whose signal sequence and mature N-terminal sequence are used in the modified CV-N polypeptide is *L. crispatus* CbsA protein. In this case, the additional amino acid sequence has an alanine as its first amino acid or a proline as its second amino acid. In other embodiments, the proline at residue 51 of SEQ ID NO:1 is substituted in the modified CV-N polypeptide. For example, the proline at residue 51 is substituted by a glycine, an alanine, a valine, a leucine, or an isoleucine. In other embodiments, the valine at residue 17 of SEQ ID NO:1 is substituted in the modified CV-N polypeptide. For example, the valine at residue 17 is substituted by an alanine, a leucine, or a serine. In other embodiments, the leucine at residue 18 of SEQ ID NO:1 is substituted by an alanine, a glycine, a valine, or an isoleucine in a modified CV-N polypeptide.

In some embodiments, the additional amino acid sequence is selected from the group consisting of AP, APV, APVT (SEQ ID NO:21), APAS (SEQ ID NO:22), APVN (SEQ ID NO:23), APVTNV (SEQ ID NO:24), and SP. One exemplary modified CV-N polypeptide has APVT (SEQ ID NO:21) as the additional amino acid sequence. Other exemplary modified CV-N polypeptides consist of the amino acid sequence of SEQ ID NO:2, SEQ ID NO:3, SEQ ID NO:4, or SEQ ID NO:5.

In other embodiments, the modified CV-N polypeptide further includes a heterologous cell wall-targeting sequence immediately to the C-terminus of the core amino acid sequence. The cell wall-targeting sequence comprises from the N-terminus to the C-terminus in the following order: a cell wall-associated sequence, the sequence of LPQ(S/A/T)(G/A), and a hydrophobic amino acid sequence. In some exemplary embodiments, the cell wall-targeting sequence comprises the sequence of LPQSG (SEQ ID NO:25), LPQAG (SEQ ID NO:26), or LPQTG (SEQ ID NO:27). In other exemplary embodiments, the cell wall-targeting sequence comprises the amino acid sequence of SEQ ID NO:11 or SEQ ID NO:12.

In some embodiments, the bacterium is a strain capable of colonizing the mucosal surface of human vagina, for example, *L. jensenii, L. gasseri, L. iners, L. casei, L. rhamnosus, L. acidophilus, L. plantarum, L. fermentum, L. vaginalis, L. fornicalis, L. johnsonii, L. paracasei, L. delbrueckii,* or *L. crispatus*. One preferred strain is *L. jensenii*. In other embodiments, the bacterium is a strain capable of colonizing the mucosal surface of human gastrointestinal tract, for example, *L. acidophilus, L. plantarum, L. casei, L. rhamnosus, L. helveticus, L. reuteri, L. fermentus, L. johnsonii, L. delbrueckii, L. salivarius, L. brevis, L. ruminis, L. amylovorus,* and *L. sake*. The claimed bacterium may transiently or constitutively expresses the modified CV-N polypeptide.

In a second aspect, the present invention relates to a modified CV-N polypeptide, which comprises a core amino acid sequence at least 90% identical to SEQ ID NO:1 and an additional amino acid sequence immediately to the N-terminus of the core amino acid sequence. The additional amino acid sequence consists of two to twenty, preferably up to fifteen, more preferably up to ten or six, amino acids, among which at least one of the first two amino acids is identical to the corresponding amino acid in the first two amino acids of a mature *Lactobacillus* protein following the cleavage of a signal sequence that is present in the precursor of the protein. The modified CV-N polypeptide is derived from a precursor polypeptide following the cleavage of the signal sequence, and specifically binds to gp120 of HIV and inhibits the infectivity of HIV.

In some embodiments, the *Lactobacillus* protein is *L. crispatus* CbsA protein. In other embodiments, the proline at residue 51 of SEQ ID NO:1 is substituted in the modified CV-N polypeptide. For example, the proline at residue 51 is substituted by a glycine, an alanine, a valine, a leucine, or an isoleucine. In other embodiments, the valine at residue 17 of SEQ ID NO:1 is substituted in the modified CV-N polypeptide. For example, the valine at residue 17 is substituted by an alanine, a leucine, or a serine. In other embodiments, the leucine at residue 18 of SEQ ID NO:1 is substituted by an alanine, a glycine, a valine, or an isoleucine in a modified CV-N polypeptide.

In some embodiments, the additional amino acid sequence is selected from the group consisting of AP, APV, APVT (SEQ ID NO:21), APAS (SEQ ID NO:22), APVN (SEQ ID NO:23), APVTNV (SEQ ID NO:24), and SP. One exemplary modified CV-N polypeptide has APVT (SEQ ID NO:21) as the additional amino acid sequence. Other exemplary modified CV-N polypeptides consist of the amino acid sequence of SEQ ID NO:2, SEQ ID NO:3, SEQ ID NO:4, or SEQ ID NO:5. Also within the scope of the present invention is a precursor polypeptide of the modified CV-N polypeptide as described above, which comprises the signal sequence at the N-terminus of the modified CV-N polypeptide.

In a third aspect, the present invention relates to a composition comprising the bacterium as described above and a physiologically acceptable carrier.

In some embodiments, the *Lactobacillus* protein whose signal sequence and mature N-terminal sequence are used in the modified CV-N polypeptide is *L. crispatus* CbsA protein. In other embodiments, the proline at residue 51 of SEQ ID NO:1 is substituted in the modified CV-N polypeptide. For example, the proline at residue 51 is substituted by a glycine, an alanine, a valine, a leucine, or an isoleucine. In other embodiments, the valine at residue 17 of SEQ ID NO:1 is substituted in the modified CV-N polypeptide. For example, the valine at residue 17 is substituted by an alanine, a leucine, or a serine. In other embodiments, the leucine at residue 18 of SEQ ID NO:1 is substituted by an alanine, a glycine, a valine, or an isoleucine in a modified CV-N polypeptide.

In some embodiments, the additional amino acid sequence is selected from the group consisting of AP, APV, APVT (SEQ ID NO:21), APAS (SEQ ID NO:22), APVN (SEQ ID NO:23), APVTNV (SEQ ID NO:24), and SP. One exemplary modified CV-N polypeptide has APVT (SEQ ID NO:21) as the additional amino acid sequence. Other exemplary modified CV-N polypeptides consist of the amino acid sequence of SEQ ID NO:2, SEQ ID NO:3, SEQ ID NO:4, or SEQ ID NO:5.

In other embodiments, the modified CV-N polypeptide further includes a heterologous cell wall-targeting sequence immediately to the C-terminus of the core amino acid sequence. The cell wall-targeting sequence comprises from the N-terminus to the C-terminus in the following order: a cell wall-associated sequence, the sequence of LPQ(S/A/T)(G/A), and a hydrophobic amino acid sequence. In some exemplary embodiments, the cell wall-targeting sequence comprises the sequence of LPQSG (SEQ ID NO:25), LPQAG (SEQ ID NO:26), or LPQTG (SEQ ID NO:27). In other exemplary embodiments, the cell wall-targeting sequence comprises the amino acid sequence of SEQ ID NO:11 or SEQ ID NO:12.

In some embodiments, the bacterium is a strain capable of colonizing the mucosal surface of human vagina, for example, *L. jensenii, L. gasseri, L. iners, L. casei, L. rhamnosus, L. acidophilus, L. plantarum, L. fermentum, L. vaginalis, L. fornicalis, L. johnsonii, L. paracasei, L. delbrueckii,* or *L. crispatus*. One preferred strain is *L. jensenii*. In other embodiments, the bacterium is a strain capable of colonizing the mucosal surface of human gastrointestinal tract, for example, *L. acidophilus, L. plantarum, L. casei, L. rhamnosus, L. helveticus, L. reuteri, L. fermentum, L. johnsonii, L. delbrueckii, L. salivarius, L. brevis, L. ruminis, L. amylovorus,* and *L. sake*. The claimed bacterium may transiently or constitutively express the modified CV-N polypeptide.

In some embodiments, the composition is formulated for oral administration, for intra-rectal administration, or for intra-vaginal administration.

In a fourth aspect, the present invention relates to a composition comprising the modified CV-N polypeptide as described above and a physiologically acceptable carrier.

In some embodiments, the *Lactobacillus* protein is *L. crispatus* CbsA protein. In other embodiments, the proline at residue 51 of SEQ ID NO:1 is substituted in the modified CV-N polypeptide. For example, the proline at residue 51 is substituted by a glycine, an alanine, a valine, a leucine, or an isoleucine. In other embodiments, the valine at residue 17 of SEQ ID NO:1 is substituted in the modified CV-N polypeptide. For example, the valine at residue 17 is substituted by an alanine, a leucine, or a serine. In other embodiments, the leucine at residue 18 of SEQ ID NO:1 is substituted by an alanine, a glycine, a valine, or an isoleucine in a modified CV-N polypeptide.

In some embodiments, the additional amino acid sequence is selected from the group consisting of AP, APV, APVT (SEQ ID NO:21), APAS (SEQ ID NO:22), APVN (SEQ ID NO:23), APVTNV (SEQ ID NO:24), and SP. One exemplary modified CV-N polypeptide has APVT (SEQ ID NO:21) as the additional amino acid sequence. Other exemplary modified CV-N polypeptides consist of the amino acid sequence of SEQ ID NO:2, SEQ ID NO:3, SEQ ID NO:4, or SEQ ID NO:5.

In some embodiments, the composition is formulated for oral administration, for intra-rectal administration, or for intra-vaginal administration.

In a fifth aspect, the present invention relates to an isolated polynucleotide sequence encoding the modified CV-N polypeptide described above, including the precursor polypeptide of the modified CV-N polypeptide.

In some embodiments, the *Lactobacillus* protein is *L. crispatus* CbsA protein. In other embodiments, the proline at residue 51 of SEQ ID NO:1 is substituted in the modified CV-N polypeptide. For example, the proline at residue 51 is substituted by a glycine, an alanine, a valine, a leucine, or an isoleucine. In other embodiments, the valine at residue 17 of SEQ ID NO:1 is substituted in the modified CV-N polypeptide. For example, the valine at residue 17 is substituted by an alanine, a leucine, or a serine. In other embodiments, the leucine at residue 18 of SEQ ID NO:1 is substituted by an alanine, a glycine, a valine, or an isoleucine in a modified CV-N polypeptide.

In some embodiments, the additional amino acid sequence is selected from the group consisting of AP, APV, APVT (SEQ ID NO:21), APAS (SEQ ID NO:22), APVN (SEQ ID NO:23), APVTNV (SEQ ID NO:24), and SP. One exemplary modified CV-N polypeptide has APVT (SEQ ID NO:21) as the additional amino acid sequence. Other exemplary modified CV-N polypeptides consist of the amino acid sequence of SEQ ID NO:2, SEQ ID NO:3, SEQ ID NO:4, or SEQ ID NO:5.

In some embodiments, the polynucleotide sequence described above is a part of an expression cassette, where the polynucleotide sequence is operably linked to a promoter. In some exemplary embodiments, the promoter directs gene expression in a *Lactobacillus* bacterium. A preferred promoter is one derived from a *Lactobacillus* bacterium, such as *L. jensenii*. Some exemplary promoter sequences include the polynucleotide sequence of SEQ ID NO:6 or SEQ ID NO:7.

In a sixth aspect, the present invention relates to a method for inhibiting HIV infection by introducing the bacterium expressing a modified CV-N polypeptide, as described above, into the vagina, rectum, or gastrointestinal tract of a human at risk of the infection in an amount sufficient to inhibit HIV infectivity.

In a seventh aspect, the present invention relates to a method for inhibiting HIV infection by administering the modified CV-N polypeptide as described above into the vagina, rectum, or gastrointestinal tract of a human at risk of the infection in an amount sufficient to inhibit HIV infectivity.

In an eighth aspect, the present invention relates to a method for recombinantly producing a modified CV-N polypeptide, comprising the steps of introducing the polynucleotide sequence as described above into a suitable host cell and culturing the cell under conditions permitting the expression of the modified CV-N polypeptide.

In some embodiments, the host cell is cultured in vitro. In other embodiments, the host cell is cultured in vivo. In some preferred embodiments, the host cell is grown in the mucosal surface of a human vagina, rectum, or gastrointestinal tract. In some embodiments, the cell is a *Lactobacillus* bacterium, for example, *L. jensenii, L. gasseri, L. iners, L. casei, L. rhamnosus, L. acidophilus, L. plantarum, L. fermentum, L. vaginalis, L. fornicalis, L. johnsonii, L. paracasei, L. delbrueckii*, or *L. crispatus*. In other embodiments, the host cell is a *Lactobacillus* bacterium selected from *L. acidophilus, L. plantarum, L. casei, L. rhamnosus, L. helveticus, L. reuteri, L. fermentus, L. johnsonii, L. delbrueckii, L. salivarius, L. brevis, L. ruminis, L. amylovorus*, and *L. sake*.

In some embodiments, the modified CV-N polypeptide is secreted. In other embodiments, the modified CV-N polypeptide is cell wall-anchored. In some embodiments, the polynucleotide sequence is operably linked to a *Lactobacillus* promoter, such as one derived from *L. jensenii*. Exemplary promoter sequences include those set forth in SEQ ID NO:6 and SEQ ID NO:7.

In a ninth aspect, the present invention relates to two novel *Lactobacillus* promoters. In particular, the invention relates to an expression cassette comprising a polynucleotide sequence encoding a protein operably linked to a promoter that has at least 90% sequence identity to SEQ ID NO:6 or SEQ ID NO:7. In some embodiments, the promoter has the polynucleotide sequence of SEQ ID NO:6 or SEQ ID NO:7.

In a tenth aspect, the present invention relates to a method for recombinantly expressing a protein in a *Lactobacillus* bacterium, comprising the step of introducing into the bacterium the expression cassette comprising a polynucleotide sequence encoding a protein operably linked to a promoter that has at least 90% sequence identity to SEQ ID NO:6 or SEQ ID NO:7. In some embodiments, the promoter has the polynucleotide sequence of SEQ ID NO:6 or SEQ ID NO:7.

In an eleventh aspect, the present invention relates to a genetically modified *Lactobacillus* bacterium, which comprises an expression cassette that comprises a polynucleotide sequence encoding a therapeutic protein operably linked to a promoter having at least 90% sequence identity to SEQ ID NO:6 or SEQ ID NO:7 and which expresses the protein. In some embodiments, the promoter has the polynucleotide sequence of SEQ ID NO:6 or SEQ ID NO:7. In other embodiments, the genetically modified bacterium transiently or constitutively expresses the therapeutic protein.

In a twelfth aspect, the present invention relates to a method for delivering a therapeutic protein to the mucosal surface of human vagina, rectum, or gastrointestinal tract, comprising the step of introducing the genetically modified *Lactobacillus* bacterium into a human. The genetically modified *Lactobacillus* bacterium comprises an expression cassette, which includes a polynucleotide sequence encoding a therapeutic protein operably linked to a promoter having at least 90% sequence identity to SEQ ID NO:6 or SEQ ID NO:7, and expresses the protein. In some embodiments, the promoter has the polynucleotide sequence of SEQ ID NO:6 or SEQ ID NO:7. In other embodiments, the genetically modified bacterium transiently or constitutively expresses the therapeutic protein.

BRIEF DESCRIPTION OF THE DRAWINGS

FIG. 2 shows proteolytic processing of *Lactobacillus*-derived CV-N. (A): schematic representation of CV-N of 101 amino acids in fusion with CbsA signal sequence (CbsAss) (SEQ ID NO:28). CV-N possesses 2 pairs of disulfide bonds that are essential for anti-HIV activities. (B): proteolytic processing of *Lactobacillus*-derived CV-N. CV-N is first synthesized as a CbsAss fusion protein (SEQ ID NO:28). Following cleavage by a signal peptidase, a mature protein is released in to extracellular milieu. Electroblotted CV-N from semi-purified wild type CV-N or CV-N (P51G) was subjected to N-terminal amino acid sequencing.

FIG. 3 shows the results of a Western blot detecting different versions of modified CV-N proteins produced by *L. jensenii*. Site-directed mutagenesis was employed to introduce conservative amino acid substitutions into the region of APVT-CV-N (P51 G) sensitive to proteolytic processing. *L. Jensenii* was transformed with the parental APVT-CV-N (P51 G) and three CV-N variant expression plasmids, and cells cultured in Rogosa broth to stationary phase. Proteins in 5 µl of cell-free conditioned medium were resolved by SDS-PAGE, and electroblotted onto a PVDF membrane for immunodetection with anti-CV-N polyclonal anitbody. There was about 50% of CV-N expressed as a full-length molecule when APVT (SEQ ID NO:21) sequence was added upstream to the CV-N coding sequence (lane 1). The truncated CV-N species expressed in the parental construct was largely absent in plasmids harboring additional mutations V17→A, V17→L, or V17→S.

FIG. 4 shows the purification of *Lactobacillus*-derived full-length (FL) APVT-CV-N (P51G) and testing of its anti-HIV activity. (A). Analyses of *Lactobacillus*-derived full-length CV-N (P51G). Transformed *L. jensenii* harboring the CV-N (P51G) expression plasmid, pOSEL CV-N (PG) with a modified signal peptide cleavage sequence, were cultured in Rogosa broth to $OD_{600}$ at 1.4. The *Lactobacillus*-derived CV-N (P51G) was isolated, following ion exchange and gel filtration chromatography. The purified proteins at three concentrations (lanes 2-4) were analyzed on Urea-Tricine-SDS-PAGE, in reference to the CV-N (P51G) reference standard (lane 1). The resolved proteins were stained with Coomassie blue. The expression of the full-length CV-N variant was confirmed by N-terminal amino acid sequencing and mass spectrometry. (B). Biological activity of purified APVT-CV-N (P51G). The anti-HIV activity was evaluated in a CCR5- and CXCR4-tropic HIV attachment inhibition assays in collaboration with the Topical Microbicides Program at Southern Research Institute, Frederick, Md. In this assay, a monolayer of MAGI-R5-LTR-β-gal or HeLa-X4-LTR-β-gal cells were treated with *Lactobacillus*-derived APVT-CV-N (P51G), or a CV-N reference standard (NIH), for 30 min prior to addition of the cell-free viruses, HIV-$1_{BaL}$ or HIV$_{IIIB}$. The cultures were incubated for 2 hr and washed. Cells at 48 hr post-infection were lysed to measure β-galactosidase activity. Compound toxicity was monitored on sister plates based on the ability of cells to metabolize the dye 3-(4,5-dimethylthiazol-2-yl)-5-(3-carboxymethoxyphenyl)-2-(4-sulfophenyl)-2H-tetrazolium (MTS) (Promega, Madison, Wis.).

Figure 5:
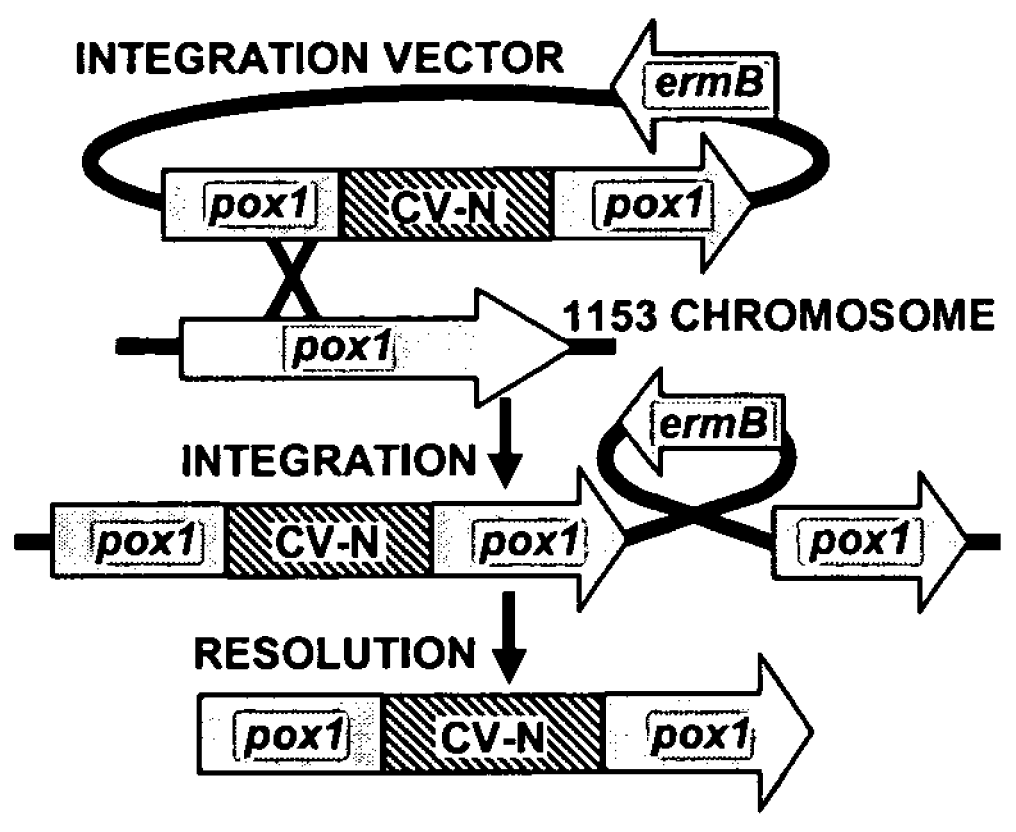

FIG. 5 illustrates the integration of genes encoding HIV-binding proteins into *L. jensenii* 1153 genome. Grey areas represent targeted chromosomal regions. Hatched areas indicate HIV binding protein expression cassette. Selected chromosomal sequences from *L. jensenii* 1153 (such as pox1) were cloned into the pUC18erm integration vector. An in-frame stop codon as well as a unique xbaI site was introduced into the middle of each insert for convenient cloning of the expression cassette (labeled CV-N). The resulting *L. jensenii* integrants were initially selected in MRS agar containing 3 μg/ml erythromycin, then resolved following continuous growth in non-selective media.

DEFINITIONS

Figure 1:
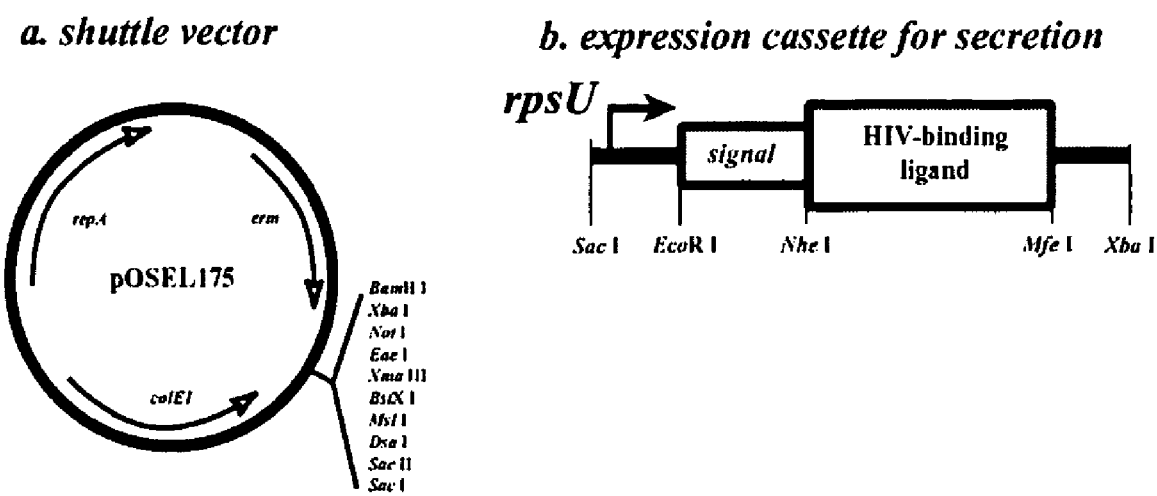
FIG. 1 is a diagram of pOSEL175, a shuttle vector between *E. coli* and *Lactobacillus* sp. (A). The repA and erm genes are derived from *L. reuteri* and the ColE1 replicon is from pBluescript. A multiple cloning site for insertion of an expression cassette (B) is located between erm and ColE1 ori.
Figure 6:
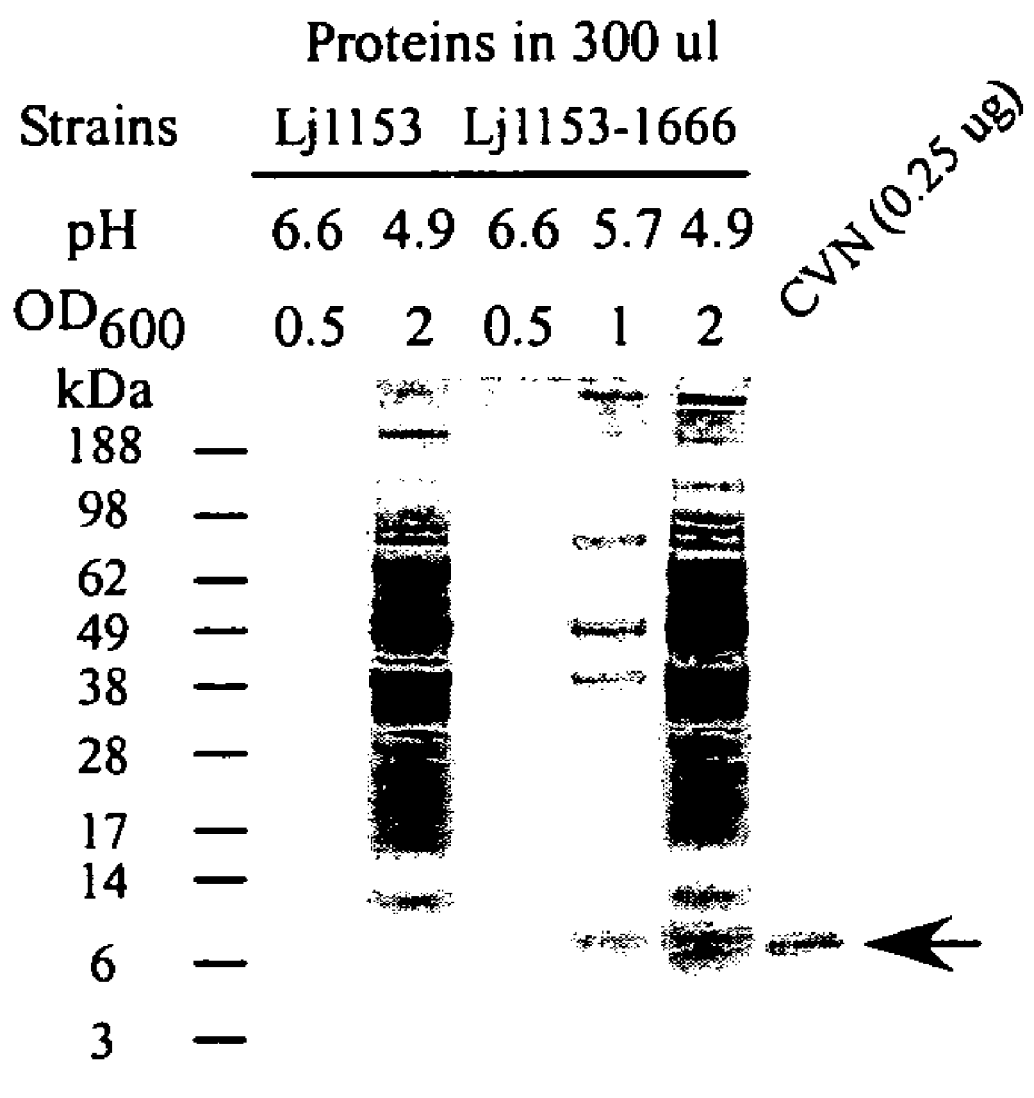
FIG. 6 shows the expression level and stability of full-length CV-N (P51G) derived from integrated and resolved *L. jensenii* strain *L. jensenii* 1153-1666, Lj1153-1666. In this strain, APVT-CV-N (P51G) expression cassette employing rpsU promoter was integrated and resolved in single copy at the pox1 site of the bacterial chromosome. The bacterial strain was cultured in Rogosa broth, in reference to the parental strain, *L. jensenii* 1153 (Lj1153). Proteins secreted into 300 μl of cell-free conditioned Rogosa media were precipitated by trichloroacetic acid (TCA), heat denatured, and resolved on reducing SDS-PAGE. Afterward, the *L. jensenii*-derived CV-N was stained with Coomassie blue R-250, in reference to the CV-N (P51G) standard (NIH).
Figure 7:
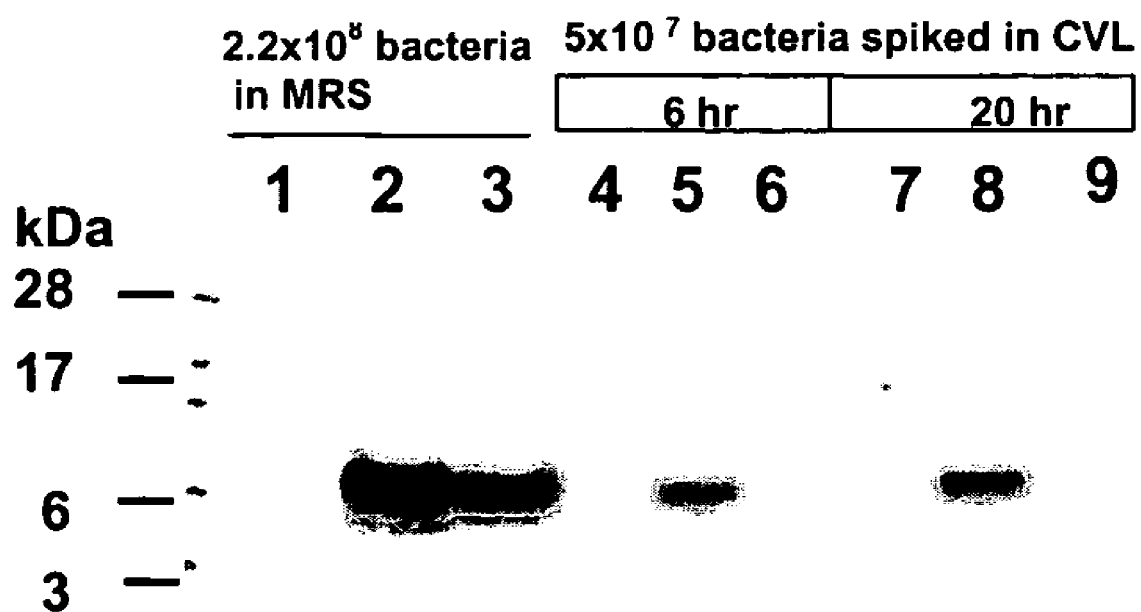
FIG. 7 shows the expression of full-length CV-N (P51G) when *L. jensenii* strains are cultured in MRS broth and cervicovaginal lavage (CVL) fluid of pigtailed macaques at 37° C., 5% CO2. The following strains were used for the evaluation: *L. jensenii* 1153 (Lj1153, lanes 1,4, and 7), *L. jensenii* 1153-1666 (Lj1153-1666, APVT-CV-N (P51G) expression cassette employing rpsU promoter integrated and resolved in single copy at the pox1 site of the bacterial chromosome, lanes 2, 5, and 8) and *L. jensenii* 1153-2666 (Lj1153-2666, APVT-CV-N (P51G) expression cassette employing ptsH promoter integrated and resolved in single copy at the pox1 site of the bacterial chromosome, lanes 3, 6, and 9). About $5 \times 10^7$ bacteria were spiked into 400 μl of CVL fluid and cultured at 37° C. and 5% CO2 for additional 6 hrs (lanes 4-6) and 20 hrs (lanes 7-9). Proteins in 10 μl cell-free supernatants were resolved on reducing SDS-PAGE and electroblotted onto a PVDF membrane for immunodetection with anti-CV-N polyclonal antibodies.

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res*. 19:5081 (1991); Ohtsuka et al., *J. Biol. Chem*. 260:2605-2608 (1985); and Rossolini et al., *Mol. Cell. Probes* 8:91-98 (1994)). The term nucleic acid is used interchangeably with gene, cDNA, or mRNA encoded by a gene.

When the relative locations of elements in a polynucleotide sequence are concerned, a "downstream" location is one at the 3' side of a reference point, and an "upstream" location is one at the 5' side of a reference point.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds. In this application, the amino acid sequence of a polypeptide is presented from the N-terminus to the C-terminus. In other words, when describing an amino acid sequence of a peptide, the first amino acid from the N-terminus is referred to as the "first amino acid."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-TUB Biochemical Nomenclature Commission. Nucleotides, likewise, may be referred to by their commonly accepted single-letter codes.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers and Miller, *Computer Applic. Biol. Sci.* 4:11-17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 70% sequence identity with a reference sequence. For instance, the core amino acid sequence in a modified CV-N polypeptide of this invention is "substantially identical" to the amino acid sequence set forth in SEQ ID NO:1. As another example, a novel *Lactobacillus* promoter of this invention is "substantially identical" to the nucleotide sequence of SEQ ID NO:6 or 7. The percent sequence identity between two "substantially identical" sequences can also be any integer from 40% to 100%. More preferred embodiments include at least: 40%, 45%, 50%, 55%, 60%, 65%, 70%, 75%, 80%, 85%, 90%, 91%, 92%, 93%, 94%, 95%, 96%, 97%, 98%, or 99% compared to a reference sequence (e.g., the amino acid sequence of SEQ ID NO:1, the polynucleotide sequence of SEQ ID NO:6 or 7) using the programs described herein, such as BLAST using standard parameters, as described below. This definition also refers to the complement of a test polynucleotide sequence, when the test sequence has substantial identity to a reference sequence.

For sequence comparison, typically one sequence acts as a reference sequence (e.g., SEQ ID NO:1, 6, or 7) to which test sequences (e.g., the core amino acid sequence of a modified CV-N polypeptide of this invention) are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform to codon preference in a specific host cell.

The term "recombinant" or "recombinantly altered" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter, a signal sequence, or a cell wall-targeting region from one source and a coding region from another source, which may be from different species or from the same species but from different proteins and associated regulatory sequences. Similarly, a heterologous protein indicates that the protein comprises two or more subsequences that are not found in the same relationship to each other in nature (e.g., a fusion protein).

An "expression cassette" is a nucleic acid, generated recombinantly or synthetically, with a series of specified nucleic acid elements that permit transcription of a particular nucleic acid in a host cell. The expression cassette can be part of a plasmid, virus, or nucleic acid fragment. Typically, the expression vector includes a nucleic acid to be transcribed operably linked to a promoter.

The phrase "specifically binds" to a specified molecule (e.g., gp120 of HIV) refers to a binding reaction in which a second molecule (e.g., the modified CV-N polypeptide of the present invention) demonstrates a high level of selectivity toward the first molecule, often in a heterogeneous population of proteins and other biologics. Thus, under designated assay conditions, the modified CV-N polypeptides bind to gp120 at least two times the background and more typically more than 10 to 100 times background.

The word "inhibit" or "inhibition," when used in the context of how the infectivity of a pathogen, e.g., HIV, is affected, refers to any detectable negative change in quantity of a parameter that reflects the ability of a pathogen to infect its host cells, compared to a standard value. The level of this negative change, for example, in the infectivity of HIV following exposure to a modified CV-N polypeptide of the present invention from the same strain of HIV not exposed to the polypeptide or exposed to only a control polypeptide having no known anti-viral activity, is preferably at least 10% or 20%, and more preferably at least 30%, 40%, 50%, 60%, 70%, 80%, or 90%, and most preferably 100%.

As used herein, the term "constitutive expression" describes the continuous or permanent expression of a gene by a cell, often referring to the expression of a heterologous gene after its introduction into a host cell. In some preferred embodiments, "constitutive expression" is the result of permanent incorporation of a heterologous gene into the host genome. In contrast, the term "transient expression" describes the expression of a gene by a cell during a limited time period, following the transformation or transfection of a host cell. In some preferred embodiments, "transient expression" is the result of the presence of the nucleic acid comprising the gene outside of the host genome, e.g., in the form of a plasmid.

A "therapeutic protein" or "therapeutic polypeptide" refers to a polypeptide possessing biological activity that can be used for the prevention and/or treatment of a disease. Examples of therapeutic polypeptides include those capable of preventing, inhibiting, stabilizing, or reversing an inherited or non-inherited genetic defect in metabolism, immune regulation, hormonal regulation, enzymatic or membrane associated structural function. For instance, a therapeutic protein can replace an absent or defective cellular protein or enzyme, or supplement production of a defective or low expressed cellular protein or enzyme. A therapeutic protein may also an antibody or protein capable of specifically bind and neutralize undesired molecules (such as an oncogene product, a molecule involved in inflammation, or any aberrantly expressed protein) or capable of inhibiting infections by harmful pathogens (such as viruses, bacteria, or fungi).

Promoters and other control elements "operably linked" to a nucleic acid sequence encoding a protein of interest are capable of affecting the expression of the gene of interest. The transcription and translation control elements need not be contiguous with the coding sequence, so long as they function to direct the expression thereof. Thus, for example, a promoter, enhancer, or terminator is "operably linked" to a coding sequence if it affects the transcription of the coding sequence.

DETAILED DESCRIPTION OF THE INVENTION

I. Introduction

The vagina and its microflora constitute a dynamic ecosystem with important host defense capabilities that promotes reproductive health. The normal vaginal flora, particularly *Lactobacillus* species, plays a key role in protecting the vagina from colonization by pathogenic microorganisms that can cause urogenital tract infections and sexually transmitted diseases. In healthy women of childbearing age, the vaginal flora is dominated by lactobacilli ($10^7$-$10^9$ CFU per gram of fluid). See, e.g., Redondo-Lopez et al., *Rev. Infect. Dis.* 12:856-872 (1990). The species of *Lactobacillus* most commonly isolated from the reproductive tracts of healthy women include *L. crispatus, L. jensenii, L. gasseri*, and *L. iners* (see, e.g., Antonio et al., *J. Infect. Dis.* 180:1950-1956 (1999); Zhou et al., *Microbiology* 150:2565-2573 (2004)). Lactobacilli are facultative anaerobes that colonize the moist mucosal surfaces of the cervix and vagina, as well as the intestinal tract and oral cavity of humans and nonhuman animals. In reproductive age women, glycogen is deposited, under estrogenic control, in the vaginal epithelium, where it is broken down to glucose by epithelial cells and bacterial enzymes. Lactobacilli metabolize the glucose to lactic acid, contributing to the maintenance of a low vaginal pH (4.0-4.5) that accounts for a major part of the non-specific defense of the vagina against urogenital pathogens. The acidity of the healthy vagina has been shown to be microbicidal for many sexually transmitted pathogens (e.g., Hanna et al., *Br. J. Obstet. Gynaecol.* 92:1267-1271 (1985), including HIV (e.g., Tevi-Benissan et al., *Clin. Diagn. Lab. Immunol.* 4:367-374 (1997)), and correlates with decreased risk for chlamydia, trichomoniasis (e.g., Hanna et al., supra), urinary tract infections (e.g., Stamey and Timothy. *J. Urol.* 114:261-263 (1975)) and infection with genital mycoplasma (e.g., Hanna et al., supra). Sperm are also rapidly inactivated at pH 4, but the presence of semen abolishes vaginal acidity for several hours, allowing an opportunity for fertilization.

Many vaginal isolates of *Lactobacillus* produce hydrogen peroxide ($H_2O_2$), a compound having broad antimicrobial and virucidal activity, which may further contribute to the inhibition of pathogens in vivo (e.g., Hawes et al., *J. Infect. Dis.* 174:1058-1063 (1996); St Amant et al., *Infect. Immun.* 70:7169-7171 (2002)). The capacity of lactobacilli to produce $H_2O_2$ is also associated with their ability to persistently colonize the vagina (e.g., Vallor et al., *J. Infect. Dis.* 184: 1431-1436 (2001)). *Lactobacillus crispatus* and *L. jensenii* are closely related phylogenetically and among the most prevalent species in the vagina. Among them, 94%-95% of them produce $H_2O_2$. These bacteria have a virucidal effect on HIV in vitro (e.g., Klebanoff and Coombs. *J. Exp. Med.* 174:289-292 (1991)). Vaginal colonization with $H_2O_2$-producing lactobacilli is correlated with a decreased incidence of HIV infection (e.g., Martin et al. *J. Infect. Dis.* 180:1863-1868 (1999); Taha et al., *AIDS* 12:1699-1706 (1998)), gonorrhea (e.g., Martin et al. supra), chlamydia (e.g., Hawes et al., supra, and bacterial vaginosis (e.g., Hawes et al., supra; Sha et al., *J. Infect. Dis.* 191:25-32 (2005)).

One approach to combat infection by pathogens (such as HIV) is the design and use of *Lactobacillus*-based microbicide. Most viruses, including HIV, enter the host at mucosal surfaces. Since the mucosa of healthy individuals is densely populated with commensal bacteria, it has been proposed that the bacterial flora on mucosal surfaces may be exploited to prevent the transmission of viruses at these sites. In this approach, vulnerable mucosal surfaces will be colonized with non-pathogenic bacteria that have been genetically modified to produce molecules that bind to and inactivate viruses, such as HIV, thereby preventing their transit through the mucosa and infection of underlying tissues. This novel approach, as described in U.S. Pat. No. 5,733,540, creates a barrier to HIV transmission that is different from, yet compatible with, current antiviral therapies and future vaccines. It is also compatible with other barrier methods, economical to produce, transparent to the user, and administration is discretely controlled by female users.

The success of the engineered *Lactobacillus*-based microbicide approach will depend, in part, on the extent and duration of colonization of the modified bacteria, and their ability to express sufficient levels of anti-viral protein. The present inventors have chosen various species of the *Lactobacillus* bacteria to deliver heterologous proteins, which have desired biological activity, to the mucosal matrix (Chang et al., supra). One preferred species used as expression host is *L. jensenii*. More particularly, *L. jensenii* 1153, a natural isolate of *L. jensenii* that colonizes the human vagina, has been used as the preferred expression host, due to its robust growth properties in vitro, ability to produce high levels of lactic acid and $H_2O_2$, and superior transformability, and ease for genetic manipulation. To facilitate genetic manipulation, a shuttle vector has been developed for introducing heterologous genes into lactobacilli. Conditions for the efficient transformation of *L. jensenii* 1153 and other strains have been further optimized.

Heterologous protein expression in *Lactobacillus* was previously accomplished. For instance, the expression of heterologous mammalian or cyanobacterial proteins, and single chain antibodies has been reported in Gram-positive bacteria, including lactobacilli, lactococci, and streptococci (e.g., Beninati et al., *Nat. Biotechnol.* 18:1060-1064 (2000); Giomarelli et al., *AIDS* 16:1351-1356 (2002); Kruger et al., *Nat. Biotechnol.* 20:702-706 (2002); Steidler et al., *Science* 289: 1352-1355 (2000); Steidler et al., *Nat. Biotechnol.* 21:785-789 (2003)). Researchers have exploited two fundamental mechanisms to express heterologous protein in these bacteria: (i) Sec-dependent machinery for protein translocation across the membrane for protein secretion (e.g., Simonen and Palva. *Microbiol. Rev.* 57:109-137 (1993)) and (ii) sortase-dependent machinery for protein anchorage to the bacterial cell wall (e.g., Navarre and Schneewind. *Microbiol. Mol. Biol. Rev.* 63:174-229 (1999)). In addition, an effort has been initiated to sequence the *L. jensenii* 1153 genome in collaboration with Lawrence Berkeley National Laboratory. The database resulting from this project has been very useful for identifying endogenous regulatory elements, to increase the efficiency of heterologous gene expression, and potential genomic integration sites. *L. jensenii* 1153 has been successfully engineered to express both secreted and cell wall-anchored forms of the prototypical HIV-1 inhibitor, two-domain CD4 (2D CD4), that adopted a functionally correct conformation and inhibited HIV infectivity in vitro (Chang et al., *Proc. Natl. Acad. Sci. USA* 100: 11672-11677 (2003)). This achievement was the first report of the expression of a complex disulfide-bonded, biologically active mammalian protein in a vaginal *Lactobacillus* and demonstrated the practical utility of genetically engineered *Lactobacillus* bacteria.

Despite the successful expression of 2D CD4 in *L.jensenii* 1153, 2D CD4 is not believed to be the optimal HIV-1 inhibitor due to its inability to inhibit many primary isolates of HIV-1. For this reason, renewed effort has been directed to cyanovirin (CV-N), a protein originally isolated from cyanobacterium, *Nostoc ellipsosporum* (Boyd et al., *Antimicrob. Agents Chemother.* 41:1521-1530 (1997); Boyd et al., U.S. Pat. No. 5,821,081). It is a relatively small, unique protein of only 11-kDa, (101 amino acids) with two domains that share significant sequence homology (Boyd et al., supra). CV-N shows potent activity against primary HIV isolates, multiple clades of HIV-1, and related retroviruses, such as simian immunodeficiency virus (SIV) and feline immunodeficiency virus (FIV) (Boyd et al., supra). In addition, CV-N has activity against other enveloped viruses, including human herpes virus 6 and measles in vitro, but no activity against adenovirus type 5 and cytomegalovirus (e.g., Dey et al., *J. Virol.* 74:4562-4569 (2000)). It can interact with both cell-free and cell-associated virus. CV-N inhibits cell-to-cell virus transmission in a co-cultivation assay, demonstrating it has activity against cell-associated HIV (Boyd et al., supra).

The molecular mechanism of CV-N activity against HIV has recently been elucidated. CV-N binds to the glycosylated form of HIV gp120 (e.g., O'Keefe et al., *Mol. Pharmacol.* 58:982-992 (2000); Shenoy et al., *J. Pharmacol. Exp. Ther.* 297:704-710 (2001)). The binding site overlaps with, but is distinct from, the site for neutralizing monoclonal antibody 2G12, which is a glycosylation-dependent epitope (e.g., Esser et al., *J. Virol.* 73:4360-4371 (1999)). Binding of CV-N at this site does not prevent binding of gp120 to soluble CD4 (sCD4) (Esser et al., supra) or conformational changes that occur in gp120 following sCD4-binding (e.g., Esser et al., supra). However, it does block CD4-dependent virus binding to cells (e.g., Esser et al., supra) and binding of gp120 to cell-associated CD4 (e.g., Dey et al., supra). In addition, CV-N inhibits sCD4-dependent binding of gp120 to cell-associated CCR5 (e.g., Dey et al., supra). CV-N binding to gp120 appears to block a membrane fusion event with the target cell that is mediated by gp120 (e.g., Dey et al., supra). This fusion event occurs within two hours after addition of virus to cells, as CV-N added at the time of inoculation (or before by pre-incubating virus with CV-N) prevented fusion (e.g., Esser et al., supra). CV-N binds to gp120 in an approximately 5:1 stoichiometry and with a $K_d$ value of 2-45 nM (O'Keefe et al., supra).

A mutant form of the CV-N polypeptide, CV-N (P51G), is of particular interest. In addition to its high potency and ability to inhibit virtually all clades of HIV-1, this CV-N mutant has demonstrated excellent stability and a propensity to exist as a monomer that readily assumes a properly refolded, native conformation (e.g., Mori et al., *Protein Expr. Purif.* 26:42-49 (2002); Barrientos et al., *J. Mol. Biol.* 325: 211-223 (2003)).

There have been no reports of production of CV-N neutralizing antibodies in animals following topical administration, and toxicity studies in rats, rabbits, and macaques have shown CV-N to be safe (Boyd et al., supra). It should be noted that the vagina's resident bacterial flora produces many proteins that are tolerated by the host. Further, the vaginal mucosa is known to be a poor immune inducer site (e.g., Johansson and Lycke, *Curr. Opin. Infect. Dis.* 16:43-49 (2003)).

The present inventors discovered, for the first time, that recombinant production of a secreted CV-N or modified CV-N polypeptide by a *Lactobacillus* bacterium is greatly facilitated by adding a signal sequence, which is originally found in a precursor of a secreted *Lactobacillus* protein (such as *L. crispatus* CbsA protein) and cleaved off to yield the mature protein. Furthermore, the inventors discovered that the proper cleavage of the recombinant signal sequence-CV-N polypeptide precursor is critical for the antiviral activity of the mature recombinant CV-N polypeptide and can be achieved by introducing to the N-terminus of the CV-N core sequence and immediately following the signal sequence an additional amino acid sequence, which has a length of 2-20 amino acids and has at least either the first or second amino acid identical to the first or second amino acid of the mature protein from whose precursor the signal sequence is derived. The inventors in addition provide two novel promoters that are particularly suitable for the purpose of recombinant protein production in *Lactobacillus* bacteria.

II. General Methodology of Molecular Biology

This invention employs routine techniques in the field of molecular biology. Basic texts disclosing the general methods useful for practicing this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides of any particular sequence may be purchased from commercial suppliers. Those that are not commercially available can be chemically synthesized according to the solid phase phosphoramidite triester method first described by Beaucage and Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of a polynucleotide, including cloned genes/regulatory elements and synthetic oligonucleotides can be verified using, e.g., the chain termination method for sequencing double-stranded templates of Wallace et al., *Gene* 16:21-26 (1981).

III. Generating Polynucleotide Sequence Encoding a Modified CV-N Protein

A. Obtaining a CV-N Coding Sequence

1. Cloning and Subcloning

The polynucleotide sequences encoding for a wild-type CV-N protein, i.e., SEQ ID NO:1, have been previously determined (Boyd et al., *Antimicrob. Agents Chemother.* 41:1521-1530 (1997)) and may be obtained from a number of laboratories that conduct research related to the protein. The coding sequence may also be chemically synthesized or obtained from a commercial supplier.

Alternatively, a nucleic acid sequence encoding a CV-N protein can be obtained from a cDNA or genomic DNA library of cyanobacteria. For example, a strain of cyanobactium, *Nostoc ellipsosporum*, can be used for as a source for cloning the CV-N gene. Standard cloning techniques such as polymerase chain reaction (PCR) using oligonucleotide primer sets based on sequence homology to the CV-N coding sequence disclosed by Boyd et al., supra, are also suitable for this purpose. Most commonly used techniques for this purpose are described in, e.g., Sambrook and Russell, supra.

2. CV-N Protein Variants

A CV-N protein variant that retains the same anti-viral activity of the wild-type protein is useful for practicing the present invention. Furthermore, to achieve improved characteristics of a recombinantly produced CV-N, such as higher yield of recombinant production of full-length protein, enhanced anti-viral activity, and resistance to degradation, modifications can also be made to a polynucleotide coding sequence.

A variety of protocols have been established and described in the art for the purpose of introducing diversity into a polypeptide. See, e.g., Zhang et al., *Proc. Natl. Acad. Sci. USA*, 94:4504-4509 (1997); and Seamer, *Nature*, 370:389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229:1193-1201 (1985)), mutagenesis using uracil-containing templates (Kunkel, *Proc. Natl. Acad. Sci. USA*, 82:488-492 (1985)), oligonucleotide-directed mutagenesis (Zoller and Smith, *Nucl. Acids Res.*, 10:6487-6500 (1982)), phosphorothioate-modified DNA mutagenesis (Taylor et al., *Nucl. Acids Res.*, 13:8749-8764 and 8765-8787 (1985)), and mutagenesis using gapped duplex DNA (Kramer et al., *Nucl. Acids Res.*, 12:9441-9456 (1984)).

By using the methods described above, a number of nucleic acids encoding CV-N variants can be derived from the wild-type sequence. Since not all modification results in a functional protein, the recombinantly produced CV-N polypeptide variants should be screened for their ability to bind gp120 and their anti-viral activity in assays described in a later section.

In addition, the polynucleotide sequence encoding a modified CV-N polypeptide can be altered to coincide with the preferred codon usage of a particular host cell, e.g., a *Lactobacillus* cell. Upon completion of the modification, the coding sequence can be subcloned into a suitable vector, for instance, an expression vector (e.g., pOSEL175), so that a CV-N variant can be recombinantly produced from the construct.

B. Recombinant Nucleic Acid Comprising Modified CV-N Coding Sequence

1. Expression Cassette

The nucleic acid encoding a modified CV-N polypeptide is typically cloned into an intermediate vector before transformation into prokaryotic or eukaryotic cells for replication and/or expression. The intermediate vector is typically a prokaryote vector such as a plasmid or shuttle vector.

To obtain high-level expression of a cloned gene, such as the DNA encoding a modified CV-N protein, one typically subclones the DNA into an expression vector that contains a strong promoter to direct transcription, a transcription/translation terminator, and a ribosome binding site for translational initiation. Numerous expression vectors utilizing prokaryotic or eukaryotic promoters are well known in the art and fully described in scientific literature such as Sambrook and Russell, supra, and Ausubel et al, supra. Viral promoters (e.g., cytomegalovirus, or CMV, promoter) can be useful for the expression of the modified CV-N. A tissue-specific promoter directing gene expression in a particular host cell type is also useful for the present invention. The modified CV-N expression may be driven by either a constitutive or inducible promoter.

Selection of the promoter used to direct expression of a heterologous nucleic acid (e.g., one encoding a CV-N variant of the present invention) depends on the particular application. The promoter is preferably positioned about the same distance from the heterologous transcription start site as it is from the transcription start site in its natural setting. As it is known in the art, however, some variation in this distance can be accommodated without loss of promoter function.

In addition to the promoter, the expression vector typically contains a transcription unit or expression cassette that contains all the additional elements required for expressing a modified CV-N in host cells. A typical expression cassette thus contains a promoter operably linked to the nucleic acid sequence encoding a CV-N variant and signals required for efficient polyadenylation of the transcript, ribosome binding sites, and translation termination. Additional elements of the cassette may also include enhancer(s).

Furthermore, the expression cassette should also contain a transcription termination region downstream of the modified CV-N gene to provide for efficient termination. The termination region may be obtained from the same gene as the promoter sequence or may be obtained from different genes.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high-yield expression systems not involving gene amplification are also suitable.

The elements that are typically included in expression vectors may also include a replicon that functions in *E. coli*, a gene encoding antibiotic resistance to permit selection of cells that harbor recombinant plasmids, and unique restriction sites in nonessential regions of the plasmid to allow insertion of exogenous sequences. The particular antibiotic resistance gene chosen is not critical, and any of the many resistance genes known in the art are suitable. The prokaryotic sequences are preferably chosen such that they do not interfere with the replication of the DNA in eukaryotic cells.

In some preferred embodiments, the expression systems used for recombinantly expressing the modified CV-N polypeptides of the present invention include promoters that direct efficient gene expression in *Lactobacillus* bacteria. Besides promoters known in the art (e.g., the $P_{23}$ promoter derived from *lactococci*, van der Vossen et al., *Appl. Environ. Microbiol.* 53:2452-2457 (1987); Chang et al., supra), the present inventors have discovered two novel strong promoters, the rpsU and ptsH promoters, from *L. jensenii*. As discussed in detail in a later section, these promoters are particularly useful for recombinantly producing CV-N variants and establishing genetically engineered *Lactobacillus* bacteria that express the CV-N variants.

2. Signal Sequence and Additional Amino Acids

In some preferred embodiments, the modified CV-N polypeptide of the present invention is recombinantly produced as a secreted protein. Proper secretion of a recombinant polypeptide requires the presence of a signal sequence that directs the cross-membrane transportation of the polypeptide following translation. Preferably, a signal sequence derived from a protein found in a *Lactobacillus* bacterium is used for practicing the present invention. For instance, a signal sequence derived from the CbsA protein from *L. crispatus*, described in WO2004/007695, can be placed in-frame upstream from the coding region of a modified CV-N polypeptide. An exemplary polynucleotide sequence encoding a CbsA signal sequence is set forth in SEQ ID NO:8. Although the newly synthesized polypeptide has the signal sequence at its N-terminus, the mature protein does not contain the signal sequence as the signal sequence is cleaved off by proteolytic activity prior to secretion of the protein.

It was unexpected to observe N-terminal truncation in *Lactobacillus*-expressed soluble CV-N. The truncated CV-N did not inhibit HIV infectivity in vitro. It has been proven beneficial to include additional polynucleotide sequence encoding one to ten amino acids between the coding regions for the signal sequence and the modified CV-N polypeptide for the purpose of obtaining a sufficient level of full-length CV-N variants. Not intended to be bound by any particular theory, the present inventors believe that the presence of such additional amino acids, especially amino acids corresponding to the N-terminal sequence of a mature protein whose precursor contains the same signal sequence used in constructing the secreted recombinant protein, can ensure that the cleavage of the signal sequence takes place at the correct location. For example, the present inventors discovered that the recombinant production of full-length CV-N variants or 2D CD4 is greatly increased when a short amino acid sequence corresponding to the N-terminus of the mature CbsA protein is introduced between the CbsA signal sequence and the CV-N sequence. In some preferred embodiments, this additional sequence comprises 2, 3, 4, 5, 6, 7, 8, 9, 10, or more amino acids (such as 11, 12, 13, 14, 15, or up to 20 amino acids) corresponding to the N-terminal sequence of the mature CbsA protein. In some cases, this additional sequence consists of the N-terminal sequence of the mature CbsA protein; in other cases, this additional sequence may include other amino acids not derived from the N-terminal sequence of the mature CbsA protein. At the minimum, either the first or second amino acid of this additional sequence is identical to the first or second amino acid of N-terminal sequence of the mature CbsA protein. In other words, the first amino acid is A and/or the second amino acid is P. Some examples of this additional sequence include AP, APV, APVT (SEQ ID NO:21), APAS (SEQ ID NO:22), APVN (SEQ ID NO:23), APVTNV (SEQ ID NO:24), and SP. A person of skill in the art would recognize that additional sequence extension could be made to these exemplary sequences without affecting the bioactivity of the modified CV-N.

3. Modification of the CV-N Sequence

In addition to the inclusion of a short amino acid sequence between the signal sequence and the CV-N sequence, the present inventors discovered that modification of the CV-N sequence may further enhance the efficiency in recombinant production, improve the stability of the protein, and therefore increase the protein's anti-viral activity. The modified CV-N polypeptide is more suitable for delivery to mucosal surfaces.

Modification at certain sites with the CV-N sequence is previously known. For instance, the proline residue at position 51 has been substituted with a glycine residue (Mori et al., supra; Barrientos et al., supra). The modified CV-N polypeptide of the present invention may further comprise modifications (e.g., addition, deletion, or substitution), particularly at positions 17, 18, and 51. In some cases, the valine at residue 17 is deleted, or substituted by another amino acid, such as an alanine, a glycine, or a serine. In some other cases, the leucine residue is substituted by another hydrophobic amino acid, such as an alanine, a glycine, a valine, or an isoleucine. In yet other cases, the proline at residue 51 is substituted by another amino acid, such as a glycine, an alanine, a valine, a leucine, or an isoleucine. Modification of other signal sequence cleavage sites by inclusion of a short amino acid sequence immediately upstream to the CV-N coding sequence to directing a full-length of protein expression in a *Lactobacillus* bacterial strain is encompassed in the scope of this invention. Various methods known to a person of skill in the art, including those mentioned in the previous section, are suitable for making the corresponding modifications in a polynucleotide sequence encoding the modified CV-N polypeptide of this invention.

4. Cell Wall-Targeting Sequence

In some preferred embodiments, the modified CV-N polypeptide of the present invention is recombinantly produce by a genetically engineered *Lactobacillus* bacterium and presented on the surface of the bacterium as a cell wall-anchored protein. To ensure that the modified CV-N polypeptide is properly attached to the bacterial cell wall, a polynucleotide sequence encoding a cell wall-targeting region is typically introduced in-frame to a location downstream from the CV-N coding sequence.

A variety of cell wall-targeting sequences are known for different host cell types. In a preferred embodiment of the present invention, a cell wall-targeting sequence suitable for *Lactobacillus* bacteria is used in constructing the expression cassette for a modified CV-N polypeptide. For a detailed description of cell wall-targeting sequences for *Lactobacillus* bacteria, see U.S. Ser. No. 10/766,993, published as US2005/0003510. Briefly, a cell wall-targeting sequence comprises from the N-terminus to C-terminus the following: (a) a cell wall-associated sequence, which may vary in length from about 40 to 1,000 amino acids, with an exemplary cell wall-associated region from *L. jensenii* being 95-amino acid long; (b) a motif of LPQ(S/A/T)(G/A), one or more copy of which may be present; and (c) a hydrophobic sequence, which is the membrane-spanning region that comprises at least 50, 60, 70, 80, 90% or more hydrophobic amino acids. In addition, a charge region may also be present at the C-terminus of a cell wall-targeting region, typically immediately following the hydrophobic sequence. This region often comprises at least 40, 50, 60, 70, 80, 90% or more charged amino acids. Two preferred cell wall-targeting sequences include those set forth in SEQ ID NO:11 and SEQ ID NO:12.

III. Expression of the Modified CV-N Protein

A. Expression Cassette for Gene Expression in *Lactobacillus* Bacteria

Recombinant gene expression in *Lactobacillus* Bacteria has been accomplished using bacterial promoters such as a lactococcal $P_{23}$ promoter (see, e.g., Chang et al., supra). This and other known promoters can be used for generating an expression cassette for expression of a gene in bacteria including *Lactobacillus* bacteria or for producing a genetically engineered *Lactobacillus* bacterial strain.

The level of gene expression under these known promoters, however, has been relatively low and thus unsatisfactory. The present inventors discovered a previously undescribed promoter derived from the *Lactobacillus* bacterial strain, *L. jens-enii*, which has demonstrated its ability to consistently drive strong expression in *Lactobacillus* bacteria. This promoter, termed rpsU promoter, is primarily derived from *L. jensenii* but also may contain artificial sequences. An exemplary sequence for this promoter is presented in SEQ ID NO:6, wherein underlined portions indicate engineered sequences.

A second previously unknown promoter from *L. jensenii*, named ptsH promoter, identified by the present inventors has an exemplary sequence set forth in SEQ ID NO:7. Similar to the rpsU promoter, the ptsH promoter may also include man-made sequences. In SEQ ID NO:7, the underlined portions represent artificial sequences.

A person of skill in the art would recognize that additional modifications could be made to the exemplary sequences without reducing the promoter's ability to direct gene expression. For instance, an artisan would recognize the important elements located at −35 and −10 of SEQ ID NO:6 or SEQ ID NO:7 and choose to preserve these elements while making promoter variants. Thus, any promoter that has a sequence substantially similar to SEQ ID NO:6 or SEQ ID NO:7 and retains its function of directing gene expression in a *Lactobacillus* bacterial strain is expressly encompassed in the scope of this invention.

The discovery of these novel promoters from *L. jensenii* makes it possible for the recombinant expression of a heterologous gene or even a gene of *Lactobacillus* origin in a *Lactobacillus* bacterial cell at a substantial level, which provides a realistic possibility for the production and use of genetically engineered *Lactobacillus* bacteria for therapeutic purposes as described above. Thus, the rpsU and pstH promoters or their functionally equivalent variants are preferred for practicing the present invention.

B. Host Cells

For the purpose of recombinantly expressing the modified CV-N polypeptide, a wide variety of host cells may be used, including prokaryotic cells (such as bacterial cells) and eukaryotic cells (such as yeast, fungal, insect, and mammalian cells). Various plant cells may also be suitable for recombinant expression. In some preferred embodiments, host cells are bacterial cells, including various strains of the *Lactobacillus* bacteria.

For the purpose of establishing a genetically engineered *Lactobacillus* bacterial strain that expresses a therapeutic protein with desired biological activity, e.g., a *Lactobacillus* bacterium constitutively expressing a modified CV-N polypeptide with anti-HIV activity, for prophylactic or therapeutic use, several strains of *Lactobacillus* bacteria are suitable for their ability to colonize the mucosal surface of human vagina or gastrointestinal tract. For example, the strains of *L. jensenii, L. gasseri, L. iners, L. casei, L. rhamnosus, L. acidophilus, L. plantarum, L. fermentum, L. vaginalis, L. fornicalis, L. johnsonii, L. paracasei, L. delbrueckii,* and *L. crispatus* are known to colonize the mucosal surface of human vagina, and the strains of *L. acidophilus, L. plantarum, L. casei, L. rhamnosus, L. helveticus, L. reuteri, L. fermentus, L. johnsonii, L. delbrueckii, L. salivarius, L. brevis, L. ruminis, L. amylovorus,* and *L. sake* are known to colonize the mucosal surface of human gastrointestinal tract. These strains are therefore preferred for practicing the present invention.

C. Transformation of Host Cells

A large variety of host cells can be potentially used for producing the modified CV-N protein of the present invention. Methods are well known for transforming these host cells, with varying efficiencies depending on the characteristics of the host cells.

There are many well-known procedures for introducing foreign nucleotide sequences into host cells. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra).

In a preferred embodiment, appropriate bacterial host strains are selected for, e.g. their transformation ability, ability for heterologous protein expression, and/or mucosal surface. The bacterial host will be rendered competent for transformation using standard techniques, such as the rubidium chloride method or electroporation (see, e.g., Wei et al., *J. Microbiol. Methods* 21:97-109 (1995).

Transformation of *L. jensenii* by electroporation can be performed by modifying standard methods as described in, e.g., Luchansky et al., *J. Dairy Sci.* 74: 3293-3302 (1991); Chang et al., supra. Briefly, freshly inoculated *L. jensenii* are cultured in MRS broth (e.g., to 0.6-0.7 at $OD_{600}$ at 37° C. and 5% $CO_2$). The bacterial cells are harvested, washed and resuspended in a cold (e.g., 4° C.) solution of sucrose and $MgCl_2$. Competent cells are then mixed with DNA and placed in a chilled gap cuvette and electroporated. Afterward, cells are allowed to recover in pre-warmed broth (e.g., for about two hours at 37° C.), prior to being plated on selective agar plate containing an antibiotic other selective agent.

Optionally, antibiotic pretreatment of the user can be used to pre-clear the mucosal surface of resident bacteria prior to introduction of the bacteria of the invention into the vagina or gastrointestinal tract. See, e.g., Freter et al., *Infect. Immun.*, 39:686-703 (1983). Antibiotics can be provided orally or can be applied directly to the vagina.

A first method involves repetitively selecting for rapid colonizing bacteria on animal or human mucosal layers. For example, one applies a wild type bacterial strain to a mucosal surface and repetitively isolates and in vitro cultures bacteria, returning at each step to the mucosal surface. Ultimately, a bacterium with an enhanced colonizing ability is obtained.

A second method involves expression of fusion proteins on the surface of recombinant bacteria. The fusion protein consists of a host-binding domain linked to a polypeptide of interest. The host-binding domain will allow the bacteria to bind to certain determinants (protein or carbohydrate) on a selected host mucosal surface with high affinity, thus conferring the bacteria a survival advantage over the resident microflora.

The third method involves induction of resident microflora to express a heterologous protein by introducing the gene via bacteriophage. A number of bacteriophage vectors have been developed for use in different bacteria. For example, a bacteriophage vector based on the temperate bacteriophage φadh can be used (see, e.g., Raya et al., *J. Bacteriol.* 174:5584-5592 (1992) and Fremaux et al., *Gene* 125:61-66 (1993)). This vector undergoes site-specific integration into the host chromosome at defined phage (attP) and bacterial (attB) attachment sites. Similarly, *Lactobacillus*-specific bacteriophage can be used to transduce vectors or other polynucleotides into the *Lactobacillus* chromosome. *Lactobacillus*-specific phage include mv4 (Auvray et al., *J. Bacteriol.*, 179:1837-1845 (1997)), φadh (Fremaux et al., *Gene* 126:61-66 (1993)), φgle (Kakikawa et al., *Gene* 175:157-165 (1996), and those belonged to Bradley's groups A or B in vaginal *lactobacillus* isolates (Kilic et al., *Clin. Diagn. Lab. Immunol.* 8:31-39 (2001)).

Certain agents that do not irritate mucosal epithelial cells may also be added to a unit dose of the bacteria in capsules or tablets to aid in colonization. Many bacteria on mucosal surfaces secrete capsular materials that coalesce to form a biofilm that covers the entire mucosal surface. It may be beneficial to add an enzyme that digests this biofilm material to promote penetration of the engineered bacteria into the biofilm for more successful colonization. The enzymes include DNAses, peptidases, collagenases, hyaluronidases, and other carbohydrate degrading enzymes. Antibiotics to which the engineered bacteria itself is not susceptible may also be added to decrease the number of resident bacteria on the mucosal surface in order to make room for the engineered bacteria.

IV. Purification of the Recombinantly Expressed Modified CV-N Protein

The recombinantly expressed modified CV-N polypeptide of the invention can be purified for use in functional assays, and upon proving its desired biological activity, e.g., anti-HIV activity, for use in therapeutic purposes. Such recombinant polypeptides can be purified from any suitable expression system.

The modified CV-N polypeptides of the invention (e.g., those having the amino acid sequence of SEQ ID NO:2, 3, 4, or 5) may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook and Russell, supra).

A number of procedures can be employed when recombinant polypeptides are purified. For example, proteins having established molecular adhesion properties can be reversible fused to polypeptides of the invention. With the appropriate ligand, the polypeptides can be selectively adsorbed to a purification column and then freed from the column in a relatively pure form. The fused protein is then removed by enzymatic activity. Finally the polypeptide can be purified using immunoaffinity columns.

A. Purification of Proteins from Recombinant Bacteria

When recombinant polypeptides are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The recombinant polypeptides of the present invention can also be separated from other proteins on the basis of their size, net surface charge, hydrophobicity, and affinity for ligands. In addition, antibodies raised against the polypeptides can be conjugated to column matrices and to immuno-purify the polypeptides. All of these methods are well known in the art. It will be apparent to one of skill that chromatographic techniques can be performed at any scale and using equipment from many different manufacturers (e.g., Pharmacia Biotech).

V. Assays for Anti-Viral Activity of the Modified CV-N Polypeptides

Upon purification, the recombinant CV-N polypeptide of the present invention, e.g., those having the amino acid sequence of SEQ ID NO:2, 3, 4, or 5, are tested for their desired biological activity, e.g., inhibiting HIV infectivity.

A. Binding Assays

Preliminary screens can be conducted by screening for modified CV-N polypeptides capable of binding to a pathogen or a protein derived from the pathogen that is critical for its infectivity. For instance, a recombinantly produced CV-N variant maybe tested for its ability to specifically bind to gp120 of HIV. While not intended to be bound to any particular theory, the present inventors believe that a CV-N polypeptide binds to the N-linked high mannose oligossacharides on gp120 molecule and subsequently prevent the interaction between gp120 and CD4, a critical step leading to the internalization of HIV into a CD4+ cell and the subsequent infection.

A variety of binding assays for detecting protein-protein interaction are well known in the art. Under conditions permissible for the formation of protein-protein complex, any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. The gp120 protein utilized in such assays can be naturally expressed, cloned, or synthesized.

B. Infectivity Assays Once a modified CV-N polypeptide is confirmed to able to specifically bind to a viral or bacterial protein, e.g., gp120 of HIV, its capability for inhibiting infectivity of the particular pathogen is further tested. Depending on the nature of the pathogen, different assay systems will be appropriate for such testing. Typically, an assay system designed for assessing the capability of a candidate therapeutic protein to inhibit the infectivity of a particular pathogen comprises a protein with known inhibitory activity (e.g., a wild-type CV-N polypeptide) as the positive control and a polypeptide with no known inhibitory activity as the negative control.

The infectivity of a pathogen, such as HIV, human herpes virus, or influenza virus, to susceptible cells in vitro can be performed in multiple formats, including assays based on viral attachment (Kimpton and Emerman. *J. Virol.* 66:2232-2239 (1992); Sanna et al., *Proc. Natl. Acad. Sci. USA.*

92:6439-6443 (1995); Dey et al., *J. Virol.* 77:2859-2865 (2003)), cell-to-cell viral transmission (e.g., Morner et al., *J. Virol.* 73:2343-2349 (1999)), virus-cell fusion (Gilbert et al., *J. Virol.* 64:5106-5113 (1990)), and cytopathic effect (e.g., O'Keefe et al., *Antimicrob. Agents Chemother.* 47:2518-2525 (2003)). Numerous small animal and nonhuman primate models that mimic viral transmission, replication, and pathogenesis have also been developed (e.g., Veazey et al., *Nat Med.* 9:343-346 (2003); Jennings et al., *Antimicrob. Agents Chemother.* 43:53-61 (1999)); Sidwell et al., *Antimicrob. Agents Chemother.* 45:749-757 (2001)).

VI. Pharmaceutical Formulations

The modified CV-N polypeptide having desired anti-viral activity described above or the genetically engineered *Lactobacillus* bacteria expressing the modified CV-N polypeptide can be used as therapeutics for preventing the infection by a variety of pathogens, including HIV, human herpes virus 1 and 6, measles virus, and influenza virus A and B. Thus, the present invention also provides pharmaceutical compositions comprising an effective amount of modified CV-N polypeptide or a transformed *Lactobacillus* bacterium expressing the modified CV-N polypeptide, which is produced according to the methods described above.

Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions are intended for parenteral, intranasal, topical, oral, or local administration, such as by aerosol or transdermally, for prophylactic treatment. Commonly, the pharmaceutical compositions are administered locally, e.g., deposited intra-vaginally or intra-rectally. Alternatively, the pharmaceutical compositions can be administered orally. Thus, the invention provides compositions for local and oral administration, which comprise the modified CV-N polypeptide or a *Lactobacillus* bacterium expressing the modified CV-N polypeptide dissolved or suspended in a physiologically acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like.

Delivery of engineered bacteria to a desired mucosal surface depends on the accessibility of the area and the local conditions. For example, engineered bacteria may be placed in a saline solution or in a foam for delivery onto the vaginal mucosa. Foams can include, e.g., one or more hydrophobically modified polysaccharides such as cellulosics and chitosans. Cellulosics include, for example, hydroxyethyl cellulose, hydroxypropyl cellulose, methyl cellulose, hydroxypropylmethyl cellulose, hydroxyethyl methyl cellulose, and the like. Chitosans include, for example, the following chitosan salts; chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, and the like. Foam can also include other components such as water, ethyl alcohol, isopropyl alcohol, glycerin, glycerol, propylene glycol, and sorbitol. Spermicides are optionally included in the bacterial composition.

Further examples of foams and foam delivery vehicles are described in, e.g., U.S. Pat. Nos. 5,595,980 and 4,922,928.

Alternatively, the bacteria can be delivered as a suppository or pessary. See, e.g., U.S. Pat. No. 4,322,399. In some embodiments, the bacteria of the invention are prepared in a preservation matrix such as described in U.S. Pat. Nos. 6,468,526 and 6,372,209, and are delivered in a dissolvable element made of dissolvable polymer material and/or complex carbohydrate material selected for dissolving properties, such that it remains in substantially solid form before use, and dissolves due to human body temperatures and moisture during use to release the agent material in a desired timed release and dosage. See, e.g., U.S. Pat. No. 5,529,782. The bacteria can also be delivered in a sponge delivery vehicle, such as described in U.S. Pat. No. 4,693,705, or via a tampon-like delivery tube.

In some embodiments, the bacteria are administered orally. For example, a daily dose of about $10^8$ CFU of lactobacilli can be used to restore the normal urogenital flora. See, e.g., Reid et al., *FEMS Immuno. Med. Microbiol.* 32:37-41 (2001).

In some embodiments, the physical form of the final recombinant products can be in a tablet/capsule suitable for self-insertion by women or intra-rectal administration. The physical rigidity of the product will vary, depending on mucosal environments.

In some embodiments, the bacteria can be in gastric juice resistant formulations (e.g., Stadler and Viernstein, *Int J Pharm.* 256:117-122 (2003) or in solid or semi-solid formulations. See, e.g., a preservation matrix known as GyneMatrix (U.S. Pat. No. 6,372,209) that has been used to successfully formulate *L. crispatus* CTV-05 and *L. jensenii* 1153. The GyneMatrix consists of a mixture of gelatin (14%), ascorbate (0.5%), trehalose (2.5%), skim milk (1.5%) and xylitol (6%). The formulation can also include some other components, including those that inhibit the growth of pathogens or those that promote adherence or colonization of lactobacilli.

In some embodiments, applications of engineered bacteria to a mucosal surface will need to be repeated on a regular basis; optimal dosing intervals are routine to determine, but will vary with different mucosal environments and bacterial strain. The dosing intervals can vary from once daily to once every 2-4 weeks.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

In some preferred embodiments, the compositions containing the modified CV-N polypeptide or a *Lactobacillus* bacterium expressing the modified CV-N polypeptide can be administered for prophylactic treatments. The compositions are administered to an individual at risk of infection by a pathogen, e.g., HIV, in an amount sufficient to prevent or at least reduce the likelihood of the infection and associated diseases, symptoms, or complications. An amount adequate to accomplish this is defined as a "prophylactically effective dose." Amounts effective for this use will depend on the level of the exposure to a pathogen, the nature of the pathogen, and, in some cases, the weight and general state of the individual, but generally range from about 0.5 mg to about 2,000 mg of the modified CV-N polypeptide per day for a 70 kg person, with dosages of from $10^7$ to $10^{12}$ CFU of a *Lactobacillus* bacterium expressing the modified CV-N polypeptide per day being more commonly used. Another exemplary use of a composition containing the modified CV-N polypeptide of the present invention is intra-vaginal or intra-rectal applications of 1% and 2% CV-N in aqueous gel with hydroxyethyl cellulose, which corresponded to protein solutions of 10 and 20 mg/ml.

Single or multiple administrations of the compositions can be carried out with dose levels and pattern being selected by the treating physician. In any event, the pharmaceutical formulations should provide a quantity of the modified CV-N polypeptide or a *Lactobacillus* bacterium expressing the modified CV-N polypeptide of this invention sufficient to effectively protect the individual from infection.

EXAMPLES

The following examples are provided by way of illustration only and not by way of limitation. Those of skill in the art will readily recognize a variety of non-critical parameters that could be changed or modified to yield essentially similar results.

Experimental Procedures

Bacterial Strains, Culture, and Transformation

Naturally occurring isolates of *L. jensenii, L. crispatus, L. gasseri*, and *L. casei* from vaginal swabs of healthy women of childbearing age were obtained (see, e.g., Antonio et al., supra; Chang et al., supra). All lactobacilli were routinely cultivated at 37° C. and 5% $CO_2$ in either MRS broth or Rogosa SL broth (Difco). Alternatively, chemically defined medium, like Medium 199 (Invitrogen), was also used to facilitate protein expression analysis. For shuttle plasmid construction and maintenance, the transformed *E. coli* DH12S, Top10 cells (Invitrogen), or *E. coli* carrying the pcnB to reduce the copy number of ColE1-based plasmids (e.g., Xu et al., *Plasmid* 48:49-58 (2002)) were grown in LB broth (Difco) at 37° C., supplemented with 200 μg/ml erythromycin (Chang et al., supra). After DNA sequence verification, *E. coli*-derived plasmids were transformed by electroporation into lactobacilli (Chang et al., supra). Transformed lactobacilli were routinely propagated either on MRS agar plates or liquid media containing 20 μg/ml erythromycin.

*L. jensenii* 1153 Genome Sequencing and Assembly

The genome sequence of *L. jensenii* 1153 was determined by using the whole-genome shotgun approach (e.g., Fleischmann et al. *Science* 269: 496-512 (1995)). Chromosomal DNA of *L. jensenii* 1153 was isolated essentially as described for *L. crispatus* (Sillanpaa et al., *J. Bacteriol*. 182:6440-6450 (2000)) except the chaotropic extraction step for removal of S-layer protein was not employed. The isolated genomic DNA was mechanically sheared using HydroShear (GeneMachines, San Carlos, Calif.). The resulting DNA fragments were blunt ended by T4 DNA polymerase and Klenow enzyme. To prepare 3- or 8-Kb genomic libraries, the DNA fragments at corresponding sizes were ligated into pUC18 vector and transformed into *E. coli* DH10B cell (Invitrogen). The bacterial transformants were selected on LB agar plates containing 5-bromo-4-chloro-3-indolyl-D-galactopyranoside and resulting colonies were arrayed into 96-well plates using a Q-pix robot (Genetix Ltd., UK). Purified plasmid DNA of randomly selected clones was sequenced on an ABI PRISM 3700 automated DNA sequencer (Applied Biosystems) to provide 3-fold coverage (approximately 75% sequence) of the *L. jensenii* 1153 genome. The sequence chromatographs were automatically transferred to a UNIX system for base calling and quality assessment using Phred/Phrap/Consed package. The sequence assembly was performed using the Paracel Genome Assembler or CAP4 (Paracel, Inc., Pasadena, Calif.). A total 484 contigs were assembled.

Identification of Native Strong Promoters in *L. jensenii* 1153

A combination of rational bioinformatics and random promoter trapping strategies were employed to identify native stronger *L. jensenii* promoters stronger than the $P_{23}$ promoter from *Lactococcus lactis* (van der Vossen et al., supra; Chang et al., supra). In rational bioinformatics approach, the genomic database of *L. jensenii* was mined using a computer program to identify potential promoter sequences. The criteria used to select promoter-like sequences included: 1) the presence of a consensus or degenerate $\sigma^A$ binding site (Moran et al., *Mol Gen Genet*. 186:339-46 (1982)); 2) located within 300 base pairs of a consensus ribosomal binding site; and 3) adjacent to a putative open reading frame (or operon) with an ATG or TTG start codon. The most promising sequences were amplified by PCR and then sub-cloned into shuttle vectors.

The random promoter trapping strategy was employed to accelerate the identification of even more powerful *L. jensenii* 1153 promoters. In this approach, a shuttle vector similar to pOSEL175 was constructed, containing a promoter-less enhanced green fluorescent protein (EGFP) gene downstream of an EcoRI restriction site and ribosomal binding site. The genomic DNA of *L. jensenii* was first digested with enzymes producing EcoRI-compatible ends (EcoRI, ApoI, MfeI, and Tsp509I), and then the fragments were ligated into the EcoRI site of the EGFP expression vector. The plasmids from *E. coli* colonies that emitted the brightest green fluorescence were electroporated into *L. jensenii*.

Subsequent screening by flow cytometric analysis and DNA sequencing led to identification of 6 endogenous promoters that drove expression of intracellular EGFP at higher levels than the lactococcal $P_{23}$ promoter. The ability of these endogenous promoters to drive expression of a heterologous protein, as a secreted molecule in *L. jensenii* 1153 was further examined using CV-N as a reporter molecule. The *L. jensenii* ptsH and rpsU promoters drove the expression of secreted CV-N~12- and 20-fold higher than the $P_{23}$ promoter, respectively, based on Western analysis.

These novel promoters provide fundamental tools to modulate expression levels of heterologous proteins in *Lactobacillus* bacteria and are particularly crucial in achieving desired levels of expression by such genetically modified bacteria on the mucosal surfaces.

Construction of Plasmids Designed for Expression of Heterologous Proteins

The basic shuttle vector used in these studies was pOSEL175, a modified version of pOSEL144 (Chang et al., supra), upon removal of two MfeI sites within an erythromycin resistance gene (ermB) gene. The plasmid pOSEL175 replicates in both *E. coli* and a variety of *lactobacillus* species, and is able to drive a high level expression of heterologous proteins upon insertion of a three-component modular cassette between its SacI and XbaI sites. Typically, the expression cassette designed for protein secretion contains a suitable promoter (e.g., rpsU), the signal sequence of *L. crispatus* S-layer protein ($cbsA_{SS}$) from the ribosome binding site (RBS) to the signal peptidase cleavage site (Chang et al., supra), and a gene encoding a HIV binding protein (such as CV-N or 2D CD4). Unique restriction sites, including SacI, EcoRI, NheI, MfeI, and XbaI were placed between each component from 5' to 3' ends, respectively. Amplification of each component was performed using conventional PCR and Pfu DNA polymerase.

Heterologous Expression of CV-N in *L. jensenii*

The nucleotide sequence corresponding to CV-N was recoded by assembly-PCR (Seamer et al., *Gene* 164:49-53 (1995)) to conform more closely to the optimal *lactobacillus* codon usage, which is AT rich (Pouwels and Leunissen, *Nucleic Acids Res.* 22:929-936 (1994)). The CV-N was amplified by 5'-GGAGCTAGCTTAGGTAAGTTTTCA-CAA-3' (SEQ ID NO:13) and 5'-GAGCAATTGTTATTCG-TATTTTAAAGTACCATC-3' (SEQ ID NO:14) using the recoded CV-N sequence. All the resulting PCR products were digested by respective restriction enzymes and fragments of DNA were ligated with NheI/MfeI-digested pOSEL651 (Chang et al., supra). To ensure protein secretion, a TAA stop codon was inserted at the 3' end of CV-N coding sequence. Introduction of a proline 51 to glycine (P51G) mutation was performed using site-directed mutagenesis.

Modification of Signal Sequence Cleavage Site

A short four-amino acid peptide from the mature protein native to CbsAss was added to the signal sequence to modify the cleavage site. Oligonucleotide primers corresponding to the peptide (e.g., APVT: SEQ ID NO:21) were designed (forward primer, SEQ ID NO:15, 5'-GTTTCAGCTGCTC-CAGTTACTTTAGGTAAGTTTTC-3'; reverse primer, SEQ ID NO:16, 5'-GAAAACTTACCTAAAGTAACTGGAG-CAGCTGAAAC-3). The polynucleotides corresponding to the four amino acids were inserted to the C-terminus of CbsA signal sequence by site-directed mutagenesis using Quick-Change® XL Kit (Stratagene, La Jolla, Calif.). The construct was electroporated into *L. Jensenii* for protein analysis, upon verification of nucleotide sequences.

Oligonucleotide-Directed Mutagenesis of Protease Sensitive Site

To eliminate the protease sensitive site, point mutations were generated around the truncation sites using Quick-Change® XL Site-Directed Mutagenesis Kit (Stratagene, La Jolla, Calif.). Plasmid pOSEL51426 was used as template. Mutations V17L and V17S of Val 17 were generated using the following primers:

```
(V17L)
                                          (SEQ ID NO:17)
forward: 5' CTATTCAAGGTTCACTTTTAACTTCAACTTG-3'
                                          (SEQ ID NO:18)
reverse: 5' CAAGTTGAAGTTAAAAGTGAACCTTGAATAG-3'

(V17S)
                                          (SEQ ID NO:19)
forward: 5' CTATTCAAGGTTCATCTTTAACTTCAACTTG-3'
                                          (SEQ ID NO:20)
reverse: 5' CAAGTTGAAGTTAAAGATGAACCTTGAATAG-3'
```

The mutagenic primers were designed based on a preferred codon usage in *L. jensenii*. After PCR reaction, Dpn I enzyme were added to the amplification mixture to degrade the parental plasmids. Newly synthesized plasmids were introduced into chemically competent *E. coli* Top 10 cells (Invitrogen) in LB broth supplemented with 200 μg/mi erythromycin. Plasmids were subsequently isolated for DNA sequencing (Biotech Core, Mountain View, Calif.) to identify clones with the desired mutations. Following verification of DNA sequences, all the resulting plasmids were electrop orated into *L. jensenii*.

Expression of CV-N Variants in Periplasmic Spaces of *E. coli*

PCR amplified CV-N variant coding sequence was cloned into NdeI and XhoI sites of pET26b(+) which utilizes pelB signal sequence (Novagen) and subsequently transformed into BL21DE3 (Novagen) (Barrientos et al., Proteins 46:153-160 (2002)). The transformed bacterial cells were cultured at 37° C. in the presence of 50 μg/ml Kanamycin to $OD_{600}$=0.4. After 2-hr induction with 1 mM isopropyl-β-D-galactopyranoside, bacterial cells were harvested, and proteins in periplasmic spaces were released upon osmotic shock.

Production of Rabbit Polyclonal Antibody against CV-N

The *E. coli* derived and refolded CV-N, which appeared homogenous on SDS-PAGE, were used to immunize New Zealand White rabbits for antibody production (Cocalico Biologicals, Inc., Reamstown, Pa.). The specificities and titers of anti-CV-N antisera were analyzed in both Western blotting and flow cytometric analysis.

Western Analysis of CV-N Expression in *L. jensenii*

The modified lactobacilli were grown at 37° C. and 5% $CO_2$ in MRS or Rogosa SL broth buffered with 100 mM HEPES (pH 7.4). Cell-free conditioned media were collected by centrifugation (12,000×g, 10 minutes) and proteins heat denatured in SDS-PAGE loading buffer (50 mM Tris-HCl, pH 6.8, 10 mM DTT, 0.4% SDS, 6% sucrose, and 0.01% bromphenol blue) (Chang et al., supra). Afterward, soluble proteins were resolved by SDS-PAGE using a 4-12% NuPAGE system (Invitrogen), and then electroblotted on to polyvinylidine difluoride (PVDF) membranes. The blot was probed with the rabbit anti-CV-N PAb OI5. The antigen-antibody reaction was then visualized by using horseradish peroxidase conjugated secondary antibody and enhanced chemiluminescent reagents (Amersham Biosciences).

Chromosomal Integration of the CV-N Expression Cassette

In an important step toward clinical development of engineered *L. jensenii* 1153, an integration system was developed that would allow integration of the CV-N expression cassette by homologous recombination into the *L. jensenii* chromosome without integrating any extraneous (non-ligand) DNA. For this purpose, the vector pUC18erm (Kenney and Moran, *J. Bacteriol.* 169:3329-3339 (1987)) with the ermB erythromycin resistance determinant and an *E. coli* pMB1 replicon was used as the backbone. As derivatives of pUC18erm will not replicate in *L. jensenii*, any erythromycin resistant bacteria that are recovered following introduction of the plasmid should contain the chromosomally integrated plasmid in single copy.

A bioinformatic strategy was adopted for the identification of genomic sequences that are suitable for site-specific stable integration, including pox1, pepO220, orf237, int, xis, cro genes, and orf938. An integration vector used for this purpose contains an insert of pox1 genomic DNA fragment (~2.8 kb), originally cloned from *L. jensenii* 1153, into which an in-frame stop codon as well as an XbaI restriction site were introduced. The expression cassette encoding APVT-CV-N (P51G) designed for protein secretion under the control of the rpsU or ptsH promoter was amplified by PCR to include flanking XbaI sites. The resulting fragment was ligated into the XbaI site of the integration vector. Then, the plasmid was transformed into *L. jensenii* by electroporation. The transformed bacteria were plated on MRS plates containing 3 μg/ml erythromycin. Erythromycin-sensitive colonies, which arise when the plasmid has inserted into the chromosome via Campbell-type integration, were selected for further screening. The transformants were first screened by CV-N protein expression, and then the chromosomal DNA from putative integrants was examined by PCR, with both integration site-specific and CV-N-specific primers, and Southern blotting to ensure that the plasmid has integrated into the appropriate site.

To resolve the single crossover event, the integrants were grown without erythromycin selection, and then plated on non-selective MRS plates. The integrated plasmids typically resolve at a rate of approximately $2 \times 10^{-3}$. The putative resolvants were sensitive to Erythromycin, and were screened first by production of CV-N protein, and then by PCR using primers specific to both integration site and CV-N expression cassette to confirm that plasmid DNA, including antibiotic resistance markers, had been excised from the bacterial chromosome, and there was no mutation in the integrated CV-N expression cassette. Evaluation of multiple resolvants did not reveal clonal variations in their ability to secrete CV-N, nor detect any mutations in the CV-N expression cassette.

Partial Purification of *Lactobacillus*-Derived CV-N

The *L. jensenii* strains expressing CV-N variants were cultured in half-strength of Rogosa SL broth (Difco) close to stationary phase. Cell-free CV-N containing supernatants were first dialyzed against 20 mM Bis-Tris, pH 5.4 at 4° C. in 3.5-kDa cut-off dialysis membrane (Spectrum Laboratories). The dialyzed supernatants were passed over columns of SP, then Q Sepharose Fast Flow resins (Amersham Biosciences). The CV-N-containing flow through was re-dialyzed against 20 mM Tris, pH 8.8 at 4° C. in 3.5-kDa cut-off dialysis membrane. Afterward, the dialyzed supernatants were first passed over columns of SP Fast Flow resin. Then, CV-N in the flow through was bound to Q Sepharose Fast Flow resins (Amersham Biosciences) and eluted in the buffer containing 150 mM NaCl. The partially purified CV-N could be concentrated via a Centricon unit (Millipore) and fractionated in a column of Superdex 75 resin (Amersham Biosciences). Similarly, the mock samples from the control strain *L. jensenii* harboring control plasmid pOSEL175 as a result of non-specific binding to ion exchange matrixes were also prepared. The amount of eluted CV-N variants was quantified by Coomassie blue staining and HIV-1 gp120 binding assay, in reference to CV-N standard (the National Institutes of Health).

N-Terminal Amino Acid Sequencing Analysis

The partially purified *Lactobacillus*-derived CV-N variants were electrophoretically separated, blotted to polyvinylidine difluoride (PVDF) membranes, and stained with Coomassie Blue. Afterward, the PVDF membranes were destained with 50% methanol and rinsed with deionized water. N-terminal sequence analysis was performed on an Applied Biosystems sequencer (Foster City, Calif.).

Linear Matrix-Assisted Laser Desorption/Ionization (MALDI) for Nominal Molecular Weight Samples to be analyzed for nominal molecular weights were exchanged into low salt (<20 mM) buffers. Samples were then spotted onto the MALDI target with an equal volume amount of MALDI matrix (Sinapinic acid in 50% ACN/0.1% TFA, Fluka, St. Louis, Mo.) and allowed to air dry. Spectra were typically acquired for 1000-2000 shots with an accelerating voltage of 25,000 volts. Calibration with external standards results in typical mass accuracies of 0.1% (ABI 4700 TOF/TOF, Applied Biosystems, Foster City, Calif.).

Stability of Integrated and Resolved CV-N Expression Cassette in *L. jensenii* 1153 Chromosomes To evaluate the stability of integrated and resolved expression cassette, eight individual colonies of resolvants were sub-cultured in antibiotic-free MRS medium overnight. Two out of the eight colonies were sub-cultured for 2 weeks in a 3-day interval, with a total of 6 generations. Cell-free medium and cell pellets were collected from the initial eight colonies and the subsequent cultures of multiple passages for analyses.

To evaluate the stability of heterologous protein expression, Western blot was used to analyze CV-N proteins in cell-free media as described above.

To evaluate the genetic stability, cell pellets collected from the same cell culture for protein stability evaluation were used. Genomic DNA was isolated as described by Nath & Galdi (Biotechniques 19:738-40 (1995)). A fragment contains partial poxi gene and the complete CV-N expression cassette were generated by PCR using primers: poxBamF 5'-GCACGGATCCCCACCTGGCATCAAG-3' (SEQ ID NO:29) and poxBamR 5'-CTACGGATCCAGCAGCA-GATATTGC-3' (SEQ ID NO:30) using Pfu polymerase. The PCR products were subsequently purified and the DNA were sequenced (Biotech Core, Mountain View, Calif.) to confirm the integrity and stability of the expression cassette.

Analysis of EGFP Expression by Flow Cytometry

Overnight culture of *L. jensenii* 1153 harboring plasmids designed for EGFP expression under native promoters or lactococcal $P_{23}$ promoter (van der Vossen et al., supra; Chang et al., supra), and promoter-less plasmid were sub-cultured at 1:50 dilutions in erythromycin-containing MRS or Rogosa SL Broth that was buffered with 100 mM HEPES, pH 7.4. The bacteria at post-exponential phases were harvested and washed twice and suspended in phosphate buffered saline (PBS) containing 2% fetal bovine serum (FBS). The fluorescence of 20,000 labeled cells was analyzed in a FACScan system (Becton Dickinson) running with the CellQuest software. Density plot output (Side scatter or forward scatter vs. fluorescence) was obtained from modified *L. jensenii*, with those harboring a promoter-less plasmid as background control. The shift in mean fluorescence intensity between the plots was calculated using FLOWJO software (Becton Dickinson).

HIV-1 gp120 Binding Assay

The ability of *Lactobacillus*-derived CV-N to interact with HIV-1 gp120 was analyzed by a gp120 binding ELISA assay that was modified according to Moore (Moore. *AIDS Res. Hum. Retroviruses* 9:209-219 (1993)). Briefly, 96-well microtiter plates coated with sheep antibody D7324 against HIV-1 gp120 (Aalto Bio, Dublin, Ireland) at 5 µg/ml were blocked with Tris-buffered saline containing 2% non-fat milk, washed and then incubated with 10 ng/well recombinant gp120 (rgp120, Protein Sciences Corp.). After washes in Tris-buffered saline containing 0.05% Tween 20, samples containing CV-N molecules were pH adjusted to be neutral, then captured by rgp120 and bound CV-N molecules were probed by polyclonal antiserum against CV-N, then detected by horseradish peroxidase-conjugated anti-rabbit IgG (Amersham Biosciences) in the presence of 3,3',5,5' tetramethylbenzidine (Neogen Corp., Lexington, Ky.). After termination of reactions, absorbance at 450 nm was read using microplate reader (Molecular Devices, Sunnyvale, Calif.).

HIV-1 Attachment Inhibition Assay

The anti-HIV activity of *Lactobacillus*-derived CV-N was evaluated in a CXCR4-Tropic HIV-1 Attachment Inhibition Assay (e.g., Kimpton and Emerman. supra). In this assay, a monolayer of HeLa-LTR-β-gal cells were treated with lactobacillus-derived CV-N (P51G), in reference to a CV-N reference standard (NIH), for 30 min prior to addition of cell-free viruses. The cultures were incubated for 2 hr and washed. Cells at 48 hr post-infection were lysed for measuring β-galactosidase activity. Compound toxicity was monitored on sister plates using MTS dye reduction. Similarly, CCR5-Tropic HIV-1 Attachment assay (e.g., Dey et al., supra) was performed using MAGI-R5 cells and HIV-1$_{Bal}$.

Evaluation of CV-N Expression in CD1 Mouse and Cervicovaginal Lavage Fluid of Pigtailed Macaque Female, ages 4-8 week old, outbred CD-1 mice (Charles River Laboratories, Raleigh, N.C.) that were determined to be in estrus by vaginal cytology were inoculated with $10^8$ CFU of *L. jensenii* 1153-1666, *L. jensenii* 1153-2666 or PBS in a 50-µl volume intra-vaginally to evaluate CV-N expression in vivo. Twenty-four hr post inoculation, a vaginal wash was collected in approximately 50 µl of PBS. Aliquots of the vaginal washes were plated on MRS plates for microbiological analysis, and Western blots were performed directly with 10-20 µl of the wash to detect CV-N expression in vivo.

Cervicovaginal lavage (CVL) specimens of pigtailed macaques were recovered by instilling 4 ml of sterile phosphate-buffered saline. The CVL samples were centrifuged to collect cell-free supernatant for culture of CV-N-expressing strains, e.g., *L. jensenii* 1153-1666 (APVT-CV-N (P51G) expression cassette employing rpsU promoter integrated and resolved in single copy at the pox1 site of the bacterial chromosome) and *L. jensenii* 1153-2666 (APVT-CV-N (P51G) expression cassette employing ptsH promoter integrated and resolved in single copy at the pox1 site of the bacterial chromosome) at 37° C., 5% $CO_2$.

Results

Characterization of Vaginal Lactobacilli and Strain Selection

To date, the present inventors have characterized a series of 20 vaginal isolates of $H_2O_2$-producing *Lactobacillus*. These vaginal isolates are primarily comprised of species *L. crispatus, L. jensenii*, and *L. gasseri*, consistent with reports that these three species dominate the vaginal microflora of healthy women (e.g., Antonio et al., supra; Vasquez et al., *J. Clin. Microbiol.* 40:2746-2749 (2002)). *L. iners* is another dominant vaginal *Lactobacillus* species, although not easily recovered using standard microbiological methods. Individual strains of lactobacilli were either obtained from the laboratory of Dr. Sharon Hillier (University of Pittsburgh, School of Medicine), the American Type Culture Collection (ATCC), or isolated from vaginal swabs obtained from healthy women.

One of the *L. jensenii* strains obtained from Dr. Hillier, designated *L. jensenii* 1153, grew well in different media, including a chemically defined medium. Additional findings, including bile salt tolerance, adherence to HeLa cells and purified extracellular matrix proteins, e.g. fibronectin, the ability to grow over a range of temperatures (25-43° C.) in vitro, and superior transformation characteristics, demonstrated that *L. jensenii* 1153 performed better than strains available from public sources, and was an excellent choice for future development.

Genomic Sequencing

Through a collaboration with the Lawrence Berkeley National Laboratory, an attempt has been made to sequence the *L. jensenii* 1153 genome. Approximately 75% of the ~2.0 Mb genome has been sequenced to date, providing a genomic database that has been mined to identify endogenous regulatory elements for increasing the efficiency of heterologous gene expression.

Construction of Plasmids Designed for Expression of Heterologous Proteins

A basic shuttle vector, pOSEL175, was derived from the native lactobacilli plasmid pLEM7 (Fons et al., Plasmid 37:199-203 (1997)) by deleting the entire IS element and inserting the *E. coli* ColE1 origin (FIG. 1A). The plasmid pOSEL175 replicates both in *E. coli* and *L. jensenii* and is able to drive a high level expression of heterologous proteins upon insertion of a four-component modular cassette between its SacI and XbaI sites. The expression cassette designed for high-level protein secretion contains a suitable promoter (rpsU in this example), the signal sequence of *L. crispatus* S-layer protein ($cbsA_{ss}$), and a gene encoding a HIV binding protein (such as CV-N).

The $P_{23}$ promoter, derived from *Lactococcus lactis* (van der Vossen et al., supra), was initially used to drive the expression of HIV-binding proteins such as 2D CD4 (Chang et al., supra) and CV-N in *L. jensenii* 1153. Subsequently, the present inventors employed bioinformatics and promoter trapping strategies to replace the $P_{23}$ promoter with native *L. jensenii* promoters of equal or greater strength to provide a range of expression levels of heterologous proteins. The *L. jensenii* rpsU promoter was found to drive the expression of secreted CV-N at least 20-fold higher than the $P_{23}$ promoter, based on Western analysis and gp120 capture ELISA (data not shown), and is now employed in the optimized CV-N expression cassette.

Expression of Secreted CV-N Protein by *L. jensenii* 1153

Cyanovirin-N (CV-N), a potent HIV-binding protein, is produced naturally by cyanobacterium and lacks any close human homologues. CV-N exhibits highly potent anti-HIV-1 activity with an $IC_{50}$ in the low nM range against virtually all clades of HIV, thus making it most attractive as a potential microbicide (Boyd et al., supra). An effective CV-N-based microbicide may require long-term stability or continuous delivery of the protein at mucosal sites of HIV entry. Transformed lactobacilli expressing secreted CV-N may represent the most practical and economically viable means of delivering this microbicide continuously to the vaginal mucosa. Consequently, the present inventors explored the possibility of expressing CV-N as a secreted protein in a mucosa-colonizing *Lactobacillus*.

It has been reported that mutation of proline 51 to glycine (P51G) in CV-N offers several advantages over the wild-type protein: in addition to improved anti-HIV activity, the CV-N (P51G) mutant exhibits an improved physical stability (e.g., Mori et al., supra).

Expression of Full-Length CV-N by *L. jensenii* 1153

To efficiently express CV-N in *Lactobacillus*, the nucleotide sequence of the CV-N gene was changed by assembly PCR (Seamer et al., Gene 164:49-53 (1995)) to *Lactobacillus*-preferred codons. When CV-N was initially expressed in *L. jensenii* 1153, the protein was found to be truncated at the N-terminus near position −16 (FIG. 2). The truncated protein could bind to recombinant HIV-1 gp120, but it did not inhibit HIV infectivity in vitro (data not shown).

To maximize the expression of full-length, secreted CV-N, several approaches were pursued, including: 1) use of the rpsU promoter, a native promoter of *L. jensenii*, to drive high level expression of secreted CV-N, 2) introduction of the P51G mutation into CV-N that reportedly stabilizes the protein in a monomeric form with proper folding (Mori et al., supra), 3) modification of signal peptidase cleavage site, and 4) removal of protease sensitive sites in CV-N. These approaches have been implemented successfully as discussed below. To support assay development, recombinant CV-N (P51G) was obtained from NIH as a reference standard (Mori et al., supra), as well as the expression vector for production of CV-N in *E. coli*. Polyclonal antibodies were prepared to *E. coli*-derived CV-N as a tool for Western blotting and immunofluorescence experiments.

To address whether aberrant signal peptide processing contributed to the secretion of truncated CV-N species in *L. Jensenii*, the expression cassette in pOSEL CV-N (PG) was modified to include a 4 amino acid extension ([1]APVT of mature CbsA protein, cloned from a human vaginal isolate of *L. crispatus*) immediately after the predicted signal peptidase cleavage site. The modified pOSEL APVT-CV-N (P51G) was then transformed into *L. jensenii* 1153 for protein analysis in reference to the bacteria harboring the parental pOSEL CV-N (P51G). Analysis of proteins in cell-free conditioned Rogosa media revealed abundant expression of CV-N molecules, with ratio of full-length vs. truncated species estimated at 1:1. In addition to APVT (SEQ ID NO:21), the amino acid sequences APV and AP, but not A alone, also supported expression of full-length CV-N (P51G) (Table 1). Other modifications, including SP, APAS (SEQ ID NO:22), APVN (SEQ ID NO:23), and APVTNV (SEQ ID NO:24), also supported expression of full-length CV-N (P51G) (Table 1).

To further reduce the production of truncated CV-N by *L. jensenii* 1153, amino acids in the proximity of the proteolytic processing site were mutated without affecting the hydrophobic core of the molecule, based on modeling studies of the x-ray structure (Dr. Laura Barrientos, CDC, personal communication). Among a series of mutants analyzed by Western blot, replacement of $Val^{17}$ in CV-N (P51G) with Ala, Leu, or Ser afforded expression of full-length molecules (FIG. 3).

Full-Length *Lactobacillus*-Expressed CV-N Adopts Correct Disulfide Bonding

A collaboration with Dr. Lewis Pannell (University of South Alabama) was established to characterize whether the *Lactobacillus*-derived APVT-CV-N (P51G) adopts correct disulfide bonding. Disulfide determination was performed by FAB-MS analysis (Gustafson et al., *Biochem. Biophys. Res. Commun*. 238:223-228 (1997)), following tryptic digestion of purified *Lactobacillus*-derived APVT-CV-N (P51G) and the CV-N (P51G) standard, with or without reduction of the disulfide bonds. The resulting mass spectra supports correct disulfide bridging among 4 cysteines in *Lactobacillus*-derived CV-N.

Full-Length *Lactobacillus*-Expressed CV-N Inhibits HIV Infectivity in vitro

To characterize the biological activity of *Lactobacillus*-derived APVT-CV-N, the full-length protein was purified by ion exchange chromatography (FIG. 4A), and the bioactivity evaluated for both HIV inhibition and cellular toxicity. As shown in FIG. 4B, the full-length molecule potently inhibited CCR5-tropic $HIV_{BaL}$ infection with an $IC_{50}$ of 0.3 nM and without evidence of cellular toxicity. In addition, the *Lactobacillus*-expressed molecule also inhibited CXCR4-tropic $HIV_{IIIB}$ in a HeLa-LTR-β-gal X4-tropic attachment assay with an $IC_{50}$ of less than 3 nM and without significant cellular toxicity. Similar bioactivity was observed for the APVT-CV-N V17L mutant discussed above.

Chromosomal Integration of Genes Encoding HIV-Binding Proteins

An integration system was devised that permits integration of genes encoding a HIV-binding protein, such as a modified CV-N protein of the present invention, into the *L. jensenii* chromosome by homologous recombination without integrating any extraneous (non-ligand) DNA (FIG. 5). The vector pUC18erm (Kenney and Moran, *J. Bacteriol*. 169:3329-3339 (1987)) was developed for chromosomal integration that contains the ermB erythromycin resistance determinant and an *E. coli* pMB1 replicon. Derivatives of pUC18erm will not replicate in *L. jensenii* such that erythromycin resistant bacteria recovered following introduction of the plasmid into bacteria should contain the plasmid integrated into the chromosome in single copy. The *L. jensenii* 1153 integrants are then resolved by growth on non-selective media, and clones selected without extraneous plasmid DNA, including the erythromycin resistance gene.

The strain resulting from successfully integrated and resolved APVT-CV-N (P51G) expression cassette into the pox1 site was designated *L. jensenii* 1153-1666. It exhibited growth properties similar to the parental strain in vitro. Driven by the rpsU promoter, it was estimated that the *L. jensenii* 1153-1666 (FIG. 6) secreted approximately 1.5-2 μg/ml (~137-183 nM) of CV-N at bacterial concentrations that similar to those ($10^8$ CFU) reported to exist within the vagina of healthy women. This level of CV-N expression in the vaginal mucosa should be able to significantly decrease the level of HIV particles available for infecting the host, and therefore have a major impact on the frequency of HIV transmission. A strain designated as *L. jensenii* 1153-2666 was produced similarly by integrating and resolving the APVT-CV-N (P51G) expression cassette that employs the ptsH promoter in single copy at the pox1 site of the bacterial chromosome.

In situ CV-N expression was evaluated, following intravaginal administration of CV-N-producing *Lactobacillus* in CD1 mouse. Both *L. jensenii* 1153-1666 and *L. jensenii* 1153-2666 were capable of association with epithelial cells in the vaginal lumen of CD-1 mice, and expressed full-length CV-N in vivo in this model.

The pig-tailed macaque (*Macaca nemestrina*) has been extensively utilized as a model for human vaginal/cervical physiology and response to sexually transmitted infections. The strength of the female pigtailed macaque is that the anatomy and physiology of the reproductive tract is remarkably similar to the human, including a *Lactobacillus*-dominant microflora (Patton et al., 1996. *Sex. Transm. Dis*. 23:489-493) and a regular menstrual cycle. When *L. jensenii* 1153-1666 and *L. jensenii* 1153-2666 were cultured in CVL fluid of the pig-tailed macaque at 37° C., 5% $CO_2$, and the resulting cell-free supernatants were analyzed to analyze CV-N expression by Western blot, both *L. jensenii* 1153-1666 and *L. jensenii* 1153-2666 expressed full-length CV-N, when cultured in CVL for 6 to 20 hr.

Genetic Stability of Integrated and Resolved CV-N Expression Cassette in the Bacterial Chromosome In vivo animal testing and ultimately the clinical development of *L. jensenii*-based anti-HIV microbicides require stable long-term expression of CV-N. It was observed that the expression of heterologous genes, such as 2D CD4, when integrated into the *L. jensenii* 1153 genome in single copy is stable over the course of more than 100 cell divisions (generations). To evaluate the stability of the integrated and resolved CV-N expression cassette, individual colonies were grown in antibiotic-free MRS medium and sub-cultured at three-day intervals for a period of two weeks, and evaluated by Western blot. The genomic DNA was isolated, and a DNA fragment containing portions of the poxi gene and the complete CV-N expression cassette was generated by PCR using primers: poxBamF 5'-GCACGGATCCCCACCTGGCATCAAG-3' (SEQ ID NO:29) and poxBamR 5'-CTACGGATCCAGCAGCAGATATTGC-3' (SEQ ID NO:30), and Pfu polymerase. The PCR fragment was sequenced to confirm the integrity of the expression cassette. The nucleotide sequence of the CV-N expression cassette remained intact and the CV-N expression from the stably integrated strain, *L.jensenii* 1153-1666, has remained constant over 2 weeks of continuous growth in liquid MRS media. In summary, genetically engineered *L. jensenii* can stably express full-length CV-N over a variety of conditions and for a sustained period of time.

Application of N-terminal APVT Extension to Cloning and Expression of Human Two-Domain CD4 in *L. jensenii*

The inventors sought to increase expression levels of soluble 2D CD4 by using a combination of strong endogenous promoters and CbsAss (Table 2). It was observed that the plasmids designed for expression of 2D CD4 employing both rpsU and ptsH promoters contained mutations in 2D CD4 coding sequence, when APVT sequence was not added immediately after the predicted signal peptidase cleavage site. Addition of APVT sequence extension allows cloning and expression of 2D CD4 possible in *L. jensenii* 1153, when strong rpsU and ptsH promoters were employed. A person of skill in the art would recognize that the N-terminal sequence extension could be made to the other peptides or proteins for cloning and recombinant expression.

All patents, patent applications, and other publications cited in this application, including published amino acid or polynucleotide sequences, are incorporated by reference in the entirety for all purposes.

SEQUENCE LISTING

SEQ ID NO:1 cyanovirin-N amino acid sequences (GenBank Accession No. P81180)

$^1$LGKFSQTCYNSAIQGS<u>V</u>LTSTCERTNGGYNTSSIDLNSVIENVDGSLK

WQ<u>P</u>SNFIETCRNTQLAGSSELAAECKTRAQQFVSTKINLDDHIANIDGT

LKYE

SEQ ID NO:2 modified CV-N polypeptide with APVT from *L. crispatus* CbsA protein at the N-terminus and a P51G substitution <u>APVT</u>$^1$LGKFSQTCYNSAIQGS<u>V</u>LTSTCERTNGGYNTSSDLNSVIENVDG SLKWQ<u>G</u>SNFIETCRNTQLAGSSELAAECKTRAQQFVSTKINLDDHIANI

DGTLKYE

TABLE 1

Characterizations of modified CV-N (P51G) secreted by *L. jensenii* 1153. The *Lactobacillus*-derived proteins were semi-purified and subjected to mass determination and N-terminal sequencing. Protein mass were compared with their predicted molecular weight when signal sequence cleavage sites were modified. The add-on modification sequences *A-*, *AP-*, *APV-*, *APVT-*(SEQ ID NO:21), and *APVTNV-*(SEQ ID NO:24) were derived from N-terminal sequences of mature protein native to CbsA signal sequence (CbsAss). The add-on modification sequences *SP-*, *APAS-*(SEQ ID NO:22), and *APVN-*(SEQ ID NO:23) are artificial sequences. The protein sequences from CbsAss are underlined plasmid-based expression of CV-N variants in full length has been achieved approaching 4-5 µg/ml (365-457 nM), based on Western analysis relative to NIH CV-N (P51G) reference standard. Superscripts indicate the amino acid position relative to the N-terminus in full-length CV-N.

| Modification of Signal Sequence Cleavage Site | SEQ ID NO: | Observed Mass/ Expected Mass (Dalton) | N-terminal Sequence | SEQ ID NO: |
|---|---|---|---|---|
| ...SA-$^1$CVN (P51G) | 31 | 9614.85/11060.70 | $^{16}$SVLTS ... (truncated at −16) | 40 |
| ...SA-*APVT*-$^1$CVN (P51G) | 32 | 11338.34/11342.00 | *APVT*-$^1$LGKF ... (full-length) | 41 |
| ...SA-*APV*-$^1$CVN (P51G) | 33 | 11237.37/11240.90 | *APV*-$^1$LGKF ... (full-length) | 42 |
| ...SA-*AP*-$^1$CVN (P51G) | 34 | 11144.32/11141.80 | *AP*-$^1$LGKF ... (full-length) | 43 |
| ...SA-*A*-$^1$CVN (P51G) | 35 | 9614.85/11060.70 | $^{16}$SVLTS ... (truncated at −16) | 40 |
| ...SA-*SP*-$^1$CVN (P51G) | 36 | 11157.21/11157.21 | *SP*-$^1$LGKF ... (full-length) | 44 |
| ...SA-*APAS*-$^1$CVN (P51G) | 37 | 11299.43/11299.43 | *APAS*-$^1$LGKF ... (full-length) | 45 |
| ...SA-*APVN*-$^1$CVN (P51G) | 38 | 11354.51/11354.51 | *APVN*-$^1$LGKF ... (full-length) | 46 |
| ...SA-*APVTNV*-$^1$CVN (P51G) | 39 | 11554.57/11554.57 | *APVTNV*-$^1$LGKF ... (full-length) | 46 |

TABLE 2

Application of N-terminal APVT extension to cloning and expression of human two-domain CD4 (2D CD4) in *L. jensenii* 1153. The extension of 4 amino acids ($^1$APVT (SEQ ID NO:21) of mature CbsA) immediately after the predicted signal peptidase cleavage site allowed cloning and expression of 2D CD4 possible in *L. jensenii* 1153, when strong promoters and CbsAss were employed. The 2D CD4 expression plasmids were sequenced and electroporated into *L. jensenii* 1153. The transformed bacteria were cultured in MRS or Rogosa broth to stationary phase. Proteins in aliquots of cell-free conditioned media were resolved by SDS-PAGE, and electroblotted onto a PVDF membrane for immunodetection with anti-CD4 polyclonal antibodies.

| Endogenous promoters | Cloning w/o use of APVT (SEQ ID NO:21) sequence | Expression w/o use of APVT (SEQ ID NO:21) sequence | Expression with use of APVT (SEQ ID NO:21) sequence |
|---|---|---|---|
| rpsU | No | No | Yes |
| ptsH | Yes | No | Yes |
| DnaX | Yes | Yes | N/A |

SEQ ID NO:3 modified CV-N polypeptide with APVT from *L. crispatus* CbsA protein at the N-terminus and P51G, V17A substitution <u>APVT</u>$^1$LGKFSQTCYNSAIQGS<u>A</u>LTSTCERTNGGYNTSSIDLNSVIENVDG SLKWQ<u>G</u>SNFIETCRNTQLAGSSELAAECKTRAQQFVSTKINLDDHIANIDG

TLKYE

SEQ ID NO:4 modified CV-N polypeptide with APVT from *L. crispatus* CbsA protein at the N-terminus and P51G, V17L substitution <u>APVT</u>$^1$LGKFSQTCYNSAIQGS<u>L</u>LTSTCERTNGGYNTSSIDLNSVIENVD GSLKWQ<u>G</u>SNFIETCRNTQLAGSSELAAECKTRAQQFVSTKINLDDHIAN

IDGTLKYE

SEQ ID NO:5 modified CV-N polypeptide with APVT from *L. crispatus* CbsA protein at the N-terminus and P51G, V17S substitution APVT¹LGKFSQTCYNSAIQGS<u>S</u>LTSTCERTNGGYNTSSIDLNSVIENVD
GSLKWQ<u>G</u>SNFIETCRNTQLAGSSELAAECKTRAQQFVSTKINLDDHIAN
IDGTLKYE SEQ ID NO:6 rpsU promoter sequence derived from *L. jensenii* (the underlined portion is artificial sequence; residues in bold and italicized indicate important locations in the promoter sequence. RBS: ribosome-binding site)

```
                    (-35)
5'GGTACCTTCTAAAAGAACTA TTGACGTATAAGGACC (-10)
TTTTTGGC TATAAT (+1)
TTAACTAT ATTGTTATGGCAGTACTGCCAAGAAATG (engineered RBS)
GAATTCAAGGAGGAA (translation start)
AAGACCACATG 3'
```

SEQ ID NO:7 ptsH promoter sequence derived from *L. jensenii* (the underlined portion is artificial sequence; residues in bold and italicized indicate important locations in the promoter sequence. RBS: ribosome-binding site)

```
5' GGTACCGTGCTAAGCTCTTGATTTGCCAAAGTATTTTTCTCTAGTT
AAAATAGCAGGGGTTCATTATAGAAACTTTATTATCAGAATTTATAGAA
GCTGGTGAAAAAATGGATTACGAGAGTATCTTAAATCAATTAGTTGATG
GGGAATTAACAGAATATAAGATAGAAGCTAAGGATGCTTTTGCTTTTCA
ACAGGCTCTACGAGCTTTTGGAAAAAGGACTTATATCAAGGGACGTGCC
CTTAGAGGTGGTGCAAT
                                     (-35)
TATCTACACTGCTTCAAATAGTAATGAATAAGG TTGAAAACATT (-10)       (+1)
TACATTATTGTTG TATTAAACTTATAA ACATGTTACTCTTAATAT (engineered RBS)
CGTACGGGTATTTTAAGAATTCAAGGAGGAAAA (translation start)
GACCACATG
```

SEQ ID NO:8 signal sequence of *L. crispatus* CbsA protein (polynucleotide sequence)

ATGAAGAAAAATTTAAGAATTGTTAGCGCTGCTGCTGCTGCTTTATTAG
CTGTTGCTCCTGTCGCTGCTTCAGCCGTTTCTACTGTTTCAGCT

SEQ ID NO:9 signal sequence of *L. crispatus* CbsA protein (amino acid sequence)

MKKNLRIVSAAAAALLAVAPVAASAVSTVSA

SEQ ID NO:10 amino acid sequence of *L. crispatus* CbsA protein precursor (sequence for the mature protein is indicated in bold, with ↓ indicating signal peptidase cleavage site)

MKKNLRIVSAAAAALLAVAPVAASAVSTVSA↓APVTNVTHLGNVTLPAS
GSTVNVKPNISLNTKAGSVSGAISVSFSATVDGTTANANFGVNASNPSK
IQLFKGSQEITDLNQVTEANAGDVYKVSMTNVGLNFGSQNANKKVTLNF
GSGWAARTEQDAMSHSLEVKLDKNGVVNLYQVVMDVTAKDFANPAVVTW
HNGTTGAAVTSASIQLYAGADDGKMNVSQVLAAVPVNQTKGNAYYAAQL
GSDQSNISYSNNLKDALKAAGVEVDAQGWFVAPQSFTFNLIATSNKNNA
TATLPVTVNVPNAKVTTVPSQSKTIMHNAYYYDKDAKRVGTDKLTRYNS
VTVAMNTTTINGKAYYEVIENGKATGKFINADNIDGTKRTLKHNAYVYK
TSKKRANKVTLKKGTEVTTYGGTYTFKNGKQYYKIGNNTDKTYVKASNF

SEQ ID NO:11 Cell wall targeting sequence

VTRTINVVDPITGKISTSVQTAKFTREDKNSNAGYTDPVTGKTTMNPWTP
AKQGLRAVNVEQIKGYVAKVDGNVDAVVVTPDSANMVVTITYQANKPEGQ
NITVKKDTVPDPADGIKNKDDLPDGTKYTWKEVPDVNSVGEKTGIVTVTF
PDGTSVDVKVTVYVDPVVESNRDTLSKEANTGNTNVAKAATVTSSKVESK
KTLPQTGSKTEQVGILGLAIATVGSLLGLGVN

SEQ ID NO:12 Cell wall targeting sequence

KKAEEVKNNSNATQKEVDDATNNLKQAQNDLDGQTTDKSKLDEAIKSAD
DTKSTDKYNNASDDTKSKFDEALKKAEEVKNNSNATQKEVDDATKNLKQ
AQNDLDGQTTNKDAINDAIKDANNAKGTDKYNNASDDTKSKFDDALKKA
EDVKNDSNANQKEVDDATKNLKNTLNNLKGQPAKKANLIASKDNAKIHK
QTLLPQTGTETNPLTAIGIGLMALGAGIFA

SEQ ID NO:13 CV-N primer (forward)

GGA<u>GCTAGC</u>TTAGGTAAGTTTTCACAA

SEQ ID NO:14 CV-N primer (reverse)

GAG<u>CAATTGTTA</u>TTCGTATTTTAAAGTACCATC

SEQ ID NO:15 APVT primer (forward)

GTTTCAGCT<u>GCTCCAGTTACT</u>TTAGGTAAGTTTTC

SEQ ID NO:16 APVT primer (reverse)

GAAAACTTACCTAA<u>AGTAACTGGAGC</u>AGCTGAAAC

SEQ ID NO:17 V17L primer (forward)

CTATTCAAGGTTCA<u>CT</u>TTTAACTTCAACTTG

SEQ ID NO:18 V17L primer (reverse)

CAAGTTGAAGTTAA<u>AAG</u>TGAACCTTGAATAG

SEQ ID NO:19 V17S primer (forward)

CTATTCAAGGTTCA<u>TCT</u>TTAACTTCAACTTG

SEQ ID NO:20 V17S primer (reverse)

CAAGTTGAAGTTAA<u>AGA</u>TGAACCTTGAATAG

---

What is claimed is:

1. A *Lactobacillus* bacterium expressing a modified cyanovirin-N (CV-N) polypeptide comprising a core amino acid sequence at least 90% identical to SEQ ID NO:1 and an additional amino acid sequence immediately to the N-terminus of the core amino acid sequence, wherein the additional amino acid sequence consists of two to twenty amino acids, among which at least one of the first two amino acids is identical to its corresponding amino acid in the first two amino acids of a mature *Lactobacillus* CbsA protein following the cleavage of the CbsA protein signal sequence, wherein the modified CV-N polypeptide is derived from a precursor polypeptide, which consists of, from the N-terminus, the CbsA protein signal sequence, the additional amino acid sequence, and the core amino acid sequence, following the cleavage of the CbsA protein signal sequence, and wherein the modified CV-N polypeptide specifically binds to gp 120 of human immunodeficiency virus (HIV) and inhibits the infectivity of HIV.

2. The bacterium of claim 1, wherein the additional amino acid sequence is selected from the group consisting of AP, APV, APVT (SEQ ID NO:21), APAS (SEQ ID NO:22), APVN (SEQ ID NO:23), APVTNV (SEQ ID NO:24), and SP.

3. A modified cyanovirin-N (CV-N) polypeptide comprising a core amino acid sequence at least 90% identical to SEQ ID NO:1 and an additional amino acid sequence immediately to the N-terminus of the core amino acid sequence, wherein the additional amino acid sequence consists of two to twenty amino acids, among which at least one of the first two amino acids is identical to its corresponding amino acid in the first two amino acids of a mature *Lactobacillus* CbsA protein following the cleavage of the CbsA protein signal sequence, wherein the modified CV-N polypeptide is derived from a precursor polypeptide, which consists of, from the N-terminus, the CbsA protein signal sequence, the additional amino acid sequence, and the core amino acid sequence, following the cleavage of the CbsA protein signal sequence, and wherein the modified CV-N polypeptide specifically binds to gp 120 of human immunodeficiency virus (HIV) and inhibits the infectivity of HIV.

4. The modified CV-N polypeptide of claim 3, wherein the additional amino acid sequence is selected from the group consists of AP, APV, APVT (SEQ ID NO:21), APAS (SEQ ID NO:22), APVN (SEQ ID NO:23), APVTNV (SEQ ID NO:24), and SP.

5. A precursor polypeptide of the modified CV-N polypeptide of claim 3, comprising the CbsA protein signal sequence at the N-terminus of the modified CV-N polypeptide.

6. A composition comprising the bacterium of claim 1 and a physiologically acceptable carrier.

7. A composition comprising the modified CV-N polypeptide of claim 3 and a physiologically acceptable carrier.

8. An isolated polynucleotide sequence encoding the modified CV-N polypeptide of claim 3.

9. An isolated polynucleotide sequence encoding the precursor polypeptide of claim 5.

10. An expression cassette comprising the polynucleotide sequence of claim 9 operably linked to a promoter.

11. A method for recombinantly producing a modified CV-N polypeptide, comprising the steps of introducing the polynucleotide sequence of claim 9 into a suitable host cell and culturing the cell under conditions permitting the expression of the modified CV-N polypeptide.

12. An expression cassette comprising a polynucleotide sequence encoding a protein operably linked to a promoter that has at least 90% sequence identity to SEQ ID NO:6 or SEQ ID NO:7.

13. The expression cassette of claim 12, wherein the promoter has the polynucleotide sequence of SEQ ID NO:6 or SEQ ID NO:7.

14. A method for recombinantly expressing a protein in a *Lactobacillus* bacterium, comprising the step of introducing the expression cassette of claim 12 into the bacterium.

15. A genetically modified *Lactobacillus* bacterium, which comprises an expression cassette that comprises a polynucleotide sequence encoding a therapeutic protein operably linked to a promoter having at least 90% sequence identity to SEQ ID NO:6 or SEQ ID NO:7 and which expresses the protein.

16. The bacterium of claim 15, wherein the promoter has the polynucleotide sequence of SEQ ID NO:6 or SEQ ID NO:7.

17. A method for delivering a therapeutic protein to the mucosal surface of human vagina or gastrointestinal tract, comprising the step of introducing the genetically modified *Lactobacillus* bacterium of claim 15 to a human.

* * * * *

SEQUENCE LISTING

<160> NUMBER OF SEQ ID NOS: 47

<210> SEQ ID NO 1
<211> LENGTH: 101
<212> TYPE: PRT
<213> ORGANISM: Nostoc ellipsosporum
<220> FEATURE:
<223> OTHER INFORMATION: wild-type cyanovirin-N (CV-N)

<400> SEQUENCE: 1

Leu Gly Lys Phe Ser Gln Thr Cys Tyr Asn Ser Ala Ile Gln Gly Ser
 1               5                  10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
                85                  90                  95

Thr Leu Lys Tyr Glu
            100

<210> SEQ ID NO 2
<211> LENGTH: 105
<212> TYPE: PRT
<213> ORGANISM: Artificial Sequence
<220> FEATURE:
<223> OTHER INFORMATION: Description of Artificial Sequence:modified
      cyanovirin-N (CV-N) polypeptide with APVT from
      Lactobacillus crispatum CbsA protein at the
      N-terminus and P51G substitution

<400> SEQUENCE: 2

Ala Pro Val Thr Leu Gly Lys Phe Ser Gln Thr Cys Tyr Asn Ser Ala
 1               5                  10                  15

Ile Gln Gly Ser Val Leu Thr Ser Thr Cys Glu Arg Thr Asn Gly Gly
            20                  25                  30

Tyr Asn Thr Ser Ser Ile Asp Leu Asn Ser Val Ile Glu Asn Val Asp
        35                  40                  45

Gly Ser Leu Lys Trp Gln Gly Ser Asn Phe Ile Glu Thr Cys Arg Asn
    50                  55                  60

Thr Gln Leu Ala Gly Ser Ser Glu Leu Ala Ala Glu Cys Lys Thr Arg
65                  70                  75                  80

Ala Gln Gln Phe Val Ser Thr Lys Ile Asn Leu Asp Asp His Ile Ala
                85                  90                  95

Asn Ile Asp Gly Thr Leu Lys Tyr Glu
            100                 105

<210> SEQ ID NO 3
<211> LENGTH: 105

```
<212> TYPE: PRT
<213> ORGANISM: Artificial Sequence
<220> FEATURE:
<223> OTHER INFORMATION: Description of Artificial Sequence:modified
      cyanovirin-N (CV-N) polypeptide with APVT from
      Lactobacillus crispatum CbsA protein at the
      N-terminus and P51G and V17A substitutions

<400> SEQUENCE: 3

Ala Pro Val Thr Leu Gly Lys Phe Ser Gln Thr Cys Tyr Asn Ser Ala
 1               5                  10                  15

Ile Gln Gly Ser Ala Leu Thr Ser Thr Cys Glu Arg Thr Asn Gly Gly
            20                  25                  30

Tyr Asn Thr Ser Ser Ile Asp Leu Asn Ser Val Ile Glu Asn Val Asp
        35                  40                  45

Gly Ser Leu Lys Trp Gln Gly Ser Asn Phe Ile Glu Thr Cys Arg Asn
 50                  55                  60

Thr Gln Leu Ala Gly Ser Ser Glu Leu Ala Ala Glu Cys Lys Thr Arg
 65                  70                  75                  80

Ala Gln Gln Phe Val Ser Thr Lys Ile Asn Leu Asp Asp His Ile Ala
                85                  90                  95

Asn Ile Asp Gly Thr Leu Lys Tyr Glu
            100                 105

<210> SEQ ID NO 4
<211> LENGTH: 105
<212> TYPE: PRT
<213> ORGANISM: Artificial Sequence
<220> FEATURE:
<223> OTHER INFORMATION: Description of Artificial Sequence:modified
      cyanovirin-N (CV-N) polypeptide with APVT from
      Lactobacillus crispatum CbsA protein at the
      N-terminus and P51G and V17L substitutions

<400> SEQUENCE: 4

Ala Pro Val Thr Leu Gly Lys Phe Ser Gln Thr Cys Tyr Asn Ser Ala
 1               5                  10                  15

Ile Gln Gly Ser Leu Leu Thr Ser Thr Cys Glu Arg Thr Asn Gly Gly
            20                  25                  30

Tyr Asn Thr Ser Ser Ile Asp Leu Asn Ser Val Ile Glu Asn Val Asp
        35                  40                  45

Gly Ser Leu Lys Trp Gln Gly Ser Asn Phe Ile Glu Thr Cys Arg Asn
 50                  55                  60

Thr Gln Leu Ala Gly Ser Ser Glu Leu Ala Ala Glu Cys Lys Thr Arg
 65                  70                  75                  80

Ala Gln Gln Phe Val Ser Thr Lys Ile Asn Leu Asp Asp His Ile Ala
                85                  90                  95

Asn Ile Asp Gly Thr Leu Lys Tyr Glu
            100                 105

<210> SEQ ID NO 5
<211> LENGTH: 105
<212> TYPE: PRT
<213> ORGANISM: Artificial Sequence
<220> FEATURE:
<223> OTHER INFORMATION: Description of Artificial Sequence:modified
      cyanovirin-N (CV-N) polypeptide with APVT from
      Lactobacillus crispatum CbsA protein at the
      N-terminus and P51G and V17S substitutions

<400> SEQUENCE: 5

Ala Pro Val Thr Leu Gly Lys Phe Ser Gln Thr Cys Tyr Asn Ser Ala
```

```
                1               5              10              15
            Ile Gln Gly Ser Ser Leu Thr Ser Thr Cys Glu Arg Thr Asn Gly Gly
                           20                      25                      30

Tyr Asn Thr Ser Ser Ile Asp Leu Asn Ser Val Ile Glu Asn Val Asp
                           35                      40                      45

Gly Ser Leu Lys Trp Gln Gly Ser Asn Phe Ile Glu Thr Cys Arg Asn
                       50                      55                      60

Thr Gln Leu Ala Gly Ser Ser Glu Leu Ala Ala Glu Cys Lys Thr Arg
                65                      70                      75                      80

Ala Gln Gln Phe Val Ser Thr Lys Ile Asn Leu Asp Asp His Ile Ala
                                   85                      90                      95

Asn Ile Asp Gly Thr Leu Lys Tyr Glu
                           100                     105
```

<210> SEQ ID NO 6
<211> LENGTH: 112
<212> TYPE: DNA
<213> ORGANISM: Artificial Sequence
<220> FEATURE:
<223> OTHER INFORMATION: Description of Artificial Sequence:Lactobacillus
      jensenii rpsU promoter with engineered
      ribosome-binding site (RBS)

<400> SEQUENCE: 6

```
ggtaccttct aaaagaacta ttgacgtata aggacctttt tggctataat ttaactatat    60
tgttatggca gtactgccaa gaaatggaat tcaaggagga aaagaccaca tg           112
```

<210> SEQ ID NO 7
<211> LENGTH: 390
<212> TYPE: DNA
<213> ORGANISM: Artificial Sequence
<220> FEATURE:
<223> OTHER INFORMATION: Description of Artificial Sequence:
      Lactobacillus jensenii ptsH promoter with engineered
      ribosome-binding site (RBS)

<400> SEQUENCE: 7

```
ggtaccgtgc taagctcttg atttgccaaa gtattttct  ctagttaaaa tagcaggggt    60
tcattataga aactttatta tcagaattta tagaagctgg tgaaaaaatg gattacgaga   120
gtatcttaaa tcaattagtt gatggggaat taacagaata taagatagaa gctaaggatg   180
cttttgcttt tcaacaggct ctacgagctt ttggaaaaag gactatatc aagggacgtg   240 cccttagagg tggtgcaatt atctacactg cttcaaatag taatgaataa ggttgaaaac   300
atttacatta ttgttgtatt aaacttataa acatgttact cttaatatcg tacgggtatt   360
ttaagaattc aaggaggaaa agaccacatg                                    390
```

<210> SEQ ID NO 8
<211> LENGTH: 93
<212> TYPE: DNA
<213> ORGANISM: Artificial Sequence
<220> FEATURE:
<223> OTHER INFORMATION: Description of Artificial Sequence:
      Lactobacillus crispatus collagen-binding surface layer (S-layer)
      protein (CbsA) signal sequence

<400> SEQUENCE: 8

```
atgaagaaaa atttaagaat tgttagcgct gctgctgctg ctttattagc tgttgctcct    60
gtcgctgctt cagccgtttc tactgtttca gct                                93
```

```
<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence:
      Lactobacillus crispatus collagen-binding surface layer (S-layer)
      protein (CbsA) signal sequence

<400> SEQUENCE: 9

Met Lys Lys Asn Leu Arg Ile Val Ser Ala Ala Ala Ala Leu Leu
  1               5                  10                  15

Ala Val Ala Pro Val Ala Ala Ser Ala Val Ser Thr Val Ser Ala
                 20                  25                  30

<210> SEQ ID NO 10
<211> LENGTH: 440
<212> TYPE: PRT
<213> ORGANISM: Lactobacillus crispatus
<220> FEATURE:
<223> OTHER INFORMATION: collagen-binding surface layer (S-layer)
      protein (CbsA) precursor
<220> FEATURE:
<221> NAME/KEY: SIGNAL
<222> LOCATION: (1)..(31)
<223> OTHER INFORMATION: signal peptide sequence
<220> FEATURE:
<221> NAME/KEY: PEPTIDE
<222> LOCATION: (32)..(440)
<223> OTHER INFORMATION: collagen-binding surface layer (S-layer) mature
      protein (CbsA)

<400> SEQUENCE: 10

Met Lys Lys Asn Leu Arg Ile Val Ser Ala Ala Ala Ala Leu Leu
  1               5                  10                  15

Ala Val Ala Pro Val Ala Ala Ser Ala Val Ser Thr Val Ser Ala Ala
                 20                  25                  30

Pro Val Thr Asn Val Thr His Leu Gly Asn Val Thr Leu Pro Ala Ser
         35                  40                  45

Gly Ser Thr Val Asn Val Lys Pro Asn Ile Ser Leu Asn Thr Lys Ala
     50                  55                  60

Gly Ser Val Ser Gly Ala Ile Ser Val Ser Phe Ser Ala Thr Val Asp
 65                  70                  75                  80

Gly Thr Thr Ala Asn Ala Asn Phe Gly Val Asn Ala Ser Asn Pro Ser
                 85                  90                  95

Lys Ile Gln Leu Phe Lys Gly Ser Gln Glu Ile Thr Asp Leu Asn Gln
            100                 105                 110

Val Thr Glu Ala Asn Ala Gly Asp Val Tyr Lys Val Ser Met Thr Asn
        115                 120                 125

Val Gly Leu Asn Phe Gly Ser Gln Asn Ala Asn Lys Lys Val Thr Leu
    130                 135                 140

Asn Phe Gly Ser Gly Trp Ala Ala Arg Thr Glu Gln Asp Ala Met Ser
145                 150                 155                 160

His Ser Leu Glu Val Lys Leu Asp Lys Asn Gly Val Val Asn Leu Tyr
                165                 170                 175

Gln Val Val Met Asp Val Thr Ala Lys Asp Phe Ala Asn Pro Ala Val
            180                 185                 190

Val Thr Trp His Asn Gly Thr Thr Gly Ala Ala Val Thr Ser Ala Ser
        195                 200                 205

Ile Gln Leu Tyr Ala Gly Ala Asp Asp Gly Lys Met Asn Val Ser Gln
    210                 215                 220
```

Val Leu Ala Ala Val Pro Val Asn Gln Thr Lys Gly Asn Ala Tyr Tyr
225                 230                 235                 240

Ala Ala Gln Leu Gly Ser Asp Gln Ser Asn Ile Ser Tyr Ser Asn Asn
            245                 250                 255

Leu Lys Asp Ala Leu Lys Ala Ala Gly Val Glu Val Asp Ala Gln Gly
        260                 265                 270

Trp Phe Val Ala Pro Gln Ser Phe Thr Phe Asn Leu Ile Ala Thr Ser
    275                 280                 285

Asn Lys Asn Asn Ala Thr Ala Thr Leu Pro Val Thr Val Asn Val Pro
290                 295                 300

Asn Ala Lys Val Thr Thr Val Pro Ser Gln Ser Lys Thr Ile Met His
305                 310                 315                 320

Asn Ala Tyr Tyr Tyr Asp Lys Asp Ala Lys Arg Val Gly Thr Asp Lys
                325                 330                 335

Leu Thr Arg Tyr Asn Ser Val Thr Val Ala Met Asn Thr Thr Thr Ile
            340                 345                 350

Asn Gly Lys Ala Tyr Tyr Glu Val Ile Glu Asn Gly Lys Ala Thr Gly
        355                 360                 365

Lys Phe Ile Asn Ala Asp Asn Ile Asp Gly Thr Lys Arg Thr Leu Lys
    370                 375                 380

His Asn Ala Tyr Val Tyr Lys Thr Ser Lys Lys Arg Ala Asn Lys Val
385                 390                 395                 400

Thr Leu Lys Lys Gly Thr Glu Val Thr Thr Tyr Gly Gly Thr Tyr Thr
                405                 410                 415

Phe Lys Asn Gly Lys Gln Tyr Tyr Lys Ile Gly Asn Asn Thr Asp Lys
            420                 425                 430

Thr Tyr Val Lys Ala Ser Asn Phe
        435                 440

<210> SEQ ID NO 11
<211> LENGTH: 232
<212> TYPE: PRT
<213> ORGANISM: Artificial Sequence
<220> FEATURE:
<223> OTHER INFORMATION: Description of Artificial Sequence:cell-wall
      targeting sequence with cell wall-associated
      sequence, LPQ(S/A/T)(G/A) sequence and hydrophobic
      amino acid sequence

<400> SEQUENCE: 11

Val Thr Arg Thr Ile Asn Val Val Asp Pro Ile Thr Gly Lys Ile Ser
1               5                   10                  15

Thr Ser Val Gln Thr Ala Lys Phe Thr Arg Glu Asp Lys Asn Ser Asn
            20                  25                  30

Ala Gly Tyr Thr Asp Pro Val Thr Gly Lys Thr Thr Met Asn Pro Trp
        35                  40                  45

Thr Pro Ala Lys Gln Gly Leu Arg Ala Val Asn Val Glu Gln Ile Lys
    50                  55                  60

Gly Tyr Val Ala Lys Val Asp Gly Asn Val Asp Ala Val Val Val Thr
65                  70                  75                  80

Pro Asp Ser Ala Asn Met Val Val Thr Ile Thr Tyr Gln Ala Asn Lys
                85                  90                  95

Pro Glu Gly Gln Asn Ile Thr Val Lys Lys Asp Thr Val Pro Asp Pro
            100                 105                 110

Ala Asp Gly Ile Lys Asn Lys Asp Asp Leu Pro Asp Gly Thr Lys Tyr
        115                 120                 125

Thr Trp Lys Glu Val Pro Asp Val Asn Ser Val Gly Glu Lys Thr Gly
    130                 135                 140

Ile Val Thr Val Thr Phe Pro Asp Gly Thr Ser Val Asp Val Lys Val
145                 150                 155                 160

Thr Val Tyr Val Asp Pro Val Val Glu Ser Asn Arg Asp Thr Leu Ser
                165                 170                 175

Lys Glu Ala Asn Thr Gly Asn Thr Asn Val Ala Lys Ala Ala Thr Val
            180                 185                 190

Thr Ser Ser Lys Val Glu Ser Lys Thr Leu Pro Gln Thr Gly Ser
        195                 200                 205

Lys Thr Glu Gln Val Gly Ile Leu Gly Leu Ala Ile Ala Thr Val Gly
    210                 215                 220

Ser Leu Leu Gly Leu Gly Val Asn
225                 230

<210> SEQ ID NO 12
<211> LENGTH: 226
<212> TYPE: PRT
<213> ORGANISM: Artificial Sequence
<220> FEATURE:
<223> OTHER INFORMATION: Description of Artificial Sequence:cell-wall
      targeting sequence with cell wall-associated
      sequence, LPQ(S/A/T)(G/A) sequence and hydrophobic
      amino acid sequence

<400> SEQUENCE: 12

Lys Lys Ala Glu Glu Val Lys Asn Asn Ser Asn Ala Thr Gln Lys Glu
1               5                   10                  15

Val Asp Asp Ala Thr Asn Asn Leu Lys Gln Ala Gln Asn Asp Leu Asp
                20                  25                  30

Gly Gln Thr Thr Asp Lys Ser Lys Leu Asp Glu Ala Ile Lys Ser Ala
            35                  40                  45

Asp Asp Thr Lys Ser Thr Asp Lys Tyr Asn Asn Ala Ser Asp Asp Thr
        50                  55                  60

Lys Ser Lys Phe Asp Glu Ala Leu Lys Lys Ala Glu Glu Val Lys Asn
65                  70                  75                  80

Asn Ser Asn Ala Thr Gln Lys Glu Val Asp Asp Ala Thr Lys Asn Leu
                85                  90                  95

Lys Gln Ala Gln Asn Asp Leu Asp Gly Gln Thr Thr Asn Lys Asp Ala
            100                 105                 110

Ile Asn Asp Ala Ile Lys Asp Ala Asn Asn Ala Lys Gly Thr Asp Lys
        115                 120                 125

Tyr Asn Asn Ala Ser Asp Asp Thr Lys Ser Lys Phe Asp Asp Ala Leu
    130                 135                 140

Lys Lys Ala Glu Asp Val Lys Asn Asp Ser Asn Ala Asn Gln Lys Glu
145                 150                 155                 160

Val Asp Asp Ala Thr Lys Asn Leu Lys Asn Thr Leu Asn Asn Leu Lys
                165                 170                 175

Gly Gln Pro Ala Lys Lys Ala Asn Leu Ile Ala Ser Lys Asp Asn Ala
            180                 185                 190

Lys Ile His Lys Gln Thr Leu Leu Pro Gln Thr Gly Thr Glu Thr Asn
        195                 200                 205

Pro Leu Thr Ala Ile Gly Ile Gly Leu Met Ala Leu Gly Ala Gly Ile
    210                 215                 220

Phe Ala
225

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:CV-N
      assembly-PCR amplification forward primer

<400> SEQUENCE: 13
ggagctagct taggtaagtt ttcacaa                                          27

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:CV-N
      assembly-PCR amplification reverse primer

<400> SEQUENCE: 14
gagcaattgt tattcgtatt ttaaagtacc atc                                   33

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:APVT site-directed mutagenesis forward oligonucleotide primer

<400> SEQUENCE: 15
gtttcagctg ctccagttac tttaggtaag ttttc 35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence:APVT site-directed mutagenesis reverse oligonucleotide primer

<400> SEQUENCE: 16
gaaaacttac ctaaagtaac tggagcagct gaaac 35

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:V17L mutation forward primer for oligonucleotide-directed mutagenesis of protease sensitive site

<400> SEQUENCE: 17
ctattcaagg ttcactttta acttcaactt g 31

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:V17L mutation reverse primer for oligonucleotide-directed mutagenesis of protease sensitive site

<400> SEQUENCE: 18

-continued

```
caagttgaag ttaaaagtga accttgaata g                                    31

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:V17S
      mutation forward primer for oligonucleotide-directed
      mutagenesis of protease sensitive site

<400> SEQUENCE: 19
ctattcaagg ttcatcttta acttcaactt g                                    31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:V17S
      mutation reverse primer for oligonucleotide-directed
      mutagenesis of protease sensitive site

<400> SEQUENCE: 20
caagttgaag ttaaagatga accttgaata g                                    31

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:signal
      sequence add-on modification sequence derived from native
      N-terminal sequence of CbsA mature protein signal
      sequence (CbsAss)

<400> SEQUENCE: 21

Ala Pro Val Thr
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:signal
      sequence add-on modification artificial sequence

<400> SEQUENCE: 22

Ala Pro Ala Ser
  1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:signal
      sequence add-on modification artificial sequence

<400> SEQUENCE: 23

Ala Pro Val Asn
  1

<210> SEQ ID NO 24
<211> LENGTH: 6
<212> TYPE: PRT
```

-continued

```
<213> ORGANISM: Artificial Sequence
<220> FEATURE:
<223> OTHER INFORMATION: Description of Artificial Sequence:signal sequence
      add-on modification sequence derived from native N-terminal
      sequence of CbsA mature protein signal sequence (CbsAss)

<400> SEQUENCE: 24

Ala Pro Val Thr Asn Val
 1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence:cell
      wall-targeting sequence

<400> SEQUENCE: 25

Leu Pro Gln Ser Gly
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:cell
      wall-targeting sequence

<400> SEQUENCE: 26

Leu Pro Gln Ala Gly
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:cell
      wall-targeting sequence

<400> SEQUENCE: 27

Leu Pro Gln Thr Gly
 1               5

<210> SEQ ID NO 28
<211> LENGTH: 132
<212> TYPE: PRT
<213> ORGANISM: Artificial Sequence
<220> FEATURE:
<223> OTHER INFORMATION: Description of Artificial
      Sequence:Lactobacillus-derived cyanovirin-N (CV-N)
      fusion protein CV-N (P51G) with CbsA signal
      sequence (CbsAss)
<220> FEATURE:
<221> NAME/KEY: SIGNAL
<222> LOCATION: (1)..(31)
<223> OTHER INFORMATION: signal peptide sequence
<220> FEATURE:
<221> NAME/KEY: DISULFID
<222> LOCATION: (39)..(53)
<220> FEATURE:
<221> NAME/KEY: DISULFID
<222> LOCATION: (89)..(104)

<400> SEQUENCE: 28

Met Lys Lys Asn Leu Arg Ile Val Ser Ala Ala Ala Ala Leu Leu
 1               5                  10                  15
```

```
Ala Val Ala Pro Val Ala Ala Ser Ala Val Ser Thr Val Ser Ala Leu
            20                  25                  30

Gly Lys Phe Ser Gln Thr Cys Tyr Asn Ser Ala Ile Gln Gly Ser Val
        35                  40                  45

Leu Thr Ser Thr Cys Glu Arg Thr Asn Gly Gly Tyr Asn Thr Ser Ser
    50                  55                  60

Ile Asp Leu Asn Ser Val Ile Glu Asn Val Asp Gly Ser Leu Lys Trp
65                  70                  75                  80

Gln Gly Ser Asn Phe Ile Glu Thr Cys Arg Asn Thr Gln Leu Ala Gly
                85                  90                  95

Ser Ser Glu Leu Ala Ala Glu Cys Lys Thr Arg Ala Gln Gln Phe Val
                100                 105                 110

Ser Thr Lys Ile Asn Leu Asp Asp His Ile Ala Asn Ile Asp Gly Thr
        115                 120                 125

Leu Lys Tyr Glu
    130
```

```
<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence:PCR primer
      poxBamF for generating DNA fragment containing
      portions of pox1 gene and complete CV-N expression
      cassette

<400> SEQUENCE: 29
gcacggatcc ccacctggca tcaag                                         25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:PCR primer
      poxBamR for generating DNA fragment containing
      portions of pox1 gene and complete CV-N expression
      cassette

<400> SEQUENCE: 30
ctacggatcc agcagcagat attgc                                         25

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage
      site

<400> SEQUENCE: 31

Ser Ala Cys Val Asn
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site
```

```
<400> SEQUENCE: 32

Ser Ala Ala Pro Val Thr Cys Val Asn
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 33

Ser Ala Ala Pro Val Cys Val Asn
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 34

Ser Ala Ala Pro Cys Val Asn
  1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 35

Ser Ala Ala Cys Val Asn
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 36

Ser Ala Ser Pro Cys Val Asn
  1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 37

Ser Ala Ala Pro Ala Ser Cys Val Asn
  1               5

<210> SEQ ID NO 38
<211> LENGTH: 9
```

```
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 38

Ser Ala Ala Pro Val Asn Cys Val Asn
  1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence:modified
      CV-N (P51G) modification of signal sequence cleavage site

<400> SEQUENCE: 39

Ser Ala Ala Pro Val Thr Asn Val Cys Val Asn
  1               5                  10

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:N-terminal
      sequence (truncated at position -16)

<400> SEQUENCE: 40

Ser Val Leu Thr Ser
  1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 41

Ala Pro Val Thr Leu Gly Lys Phe
  1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 42

Ala Pro Val Leu Gly Lys Phe
  1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 43

Ala Pro Leu Gly Lys Phe
```

```
<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 44

Ser Pro Leu Gly Lys Phe
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 45

Ala Pro Ala Ser Leu Gly Lys Phe
 1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 46

Ala Pro Val Asn Leu Gly Lys Phe
 1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence (full-length)

<400> SEQUENCE: 47

Ala Pro Val Thr Asn Val Leu Gly Lys Phe
 1               5                  10
```